(12) United States Patent
Kassab

(10) Patent No.: US 12,029,539 B2
(45) Date of Patent: *Jul. 9, 2024

(54) SYSTEMS, DEVICES, AND METHODS FOR MAPPING ORGAN PROFILES

(71) Applicant: 3DT Holdings, LLC, Zionsville, IN (US)

(72) Inventor: Ghassan S. Kassab, La Jolla, CA (US)

(73) Assignee: 3DT Holdings, LLC, Zionsville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/982,342

(22) Filed: Nov. 7, 2022

(65) Prior Publication Data
US 2023/0055624 A1    Feb. 23, 2023

Related U.S. Application Data

(63) Continuation of application No. 16/565,161, filed on Sep. 9, 2019, now Pat. No. 11,490,829, which is a
(Continued)

(51) Int. Cl.
| | |
|---|---|
| *A61B 5/0538* | (2021.01) |
| *A61B 5/02* | (2006.01) |
| *A61B 5/0215* | (2006.01) |
| *A61B 5/053* | (2021.01) |
| *A61B 5/00* | (2006.01) |
(Continued)

(52) U.S. Cl.
CPC .......... *A61B 5/053* (2013.01); *A61B 5/02007* (2013.01); *A61B 5/0215* (2013.01); *A61B 5/0538* (2013.01); *A61B 5/1076* (2013.01); *A61B 5/6853* (2013.01); *A61B 2017/00026* (2013.01); *A61B 2560/0223* (2013.01)

(58) Field of Classification Search
None
See application file for complete search history.

(56) References Cited

U.S. PATENT DOCUMENTS

| | | |
|---|---|---|
| 3,896,373 A | 7/1975 | Zelby |
| 3,986,373 A | 10/1976 | Goodlaxson |
| (Continued) | | |

FOREIGN PATENT DOCUMENTS

| | | |
|---|---|---|
| CN | 102118994 A | 7/2011 |
| EP | 0486979 A1 | 5/1992 |
| (Continued) | | |

OTHER PUBLICATIONS

AU 2013243252 filed Aug. 13, 2014 Examination Report dated Nov. 9, 2016.
(Continued)

*Primary Examiner* — Meredith Weare
(74) *Attorney, Agent, or Firm* — Rutan & Tucker LLP

(57) ABSTRACT

Devices, systems, and methods for the localization of body lumen junctions and other intraluminal structure are disclosed. Various embodiments permit clinicians to identify and locate lesions and/or anatomical structures within a lumen and accurately place leads and/or devices within a lumen, through determining the intralumen conductance and/or cross-sectional area at a plurality of locations within the body lumen.

9 Claims, 14 Drawing Sheets

Related U.S. Application Data continuation of application No. 14/010,202, filed on Aug. 26, 2013, now Pat. No. 10,413,211, which is a continuation of application No. 12/522,432, filed as application No. PCT/US2008/000833 on Jan. 23, 2008, now Pat. No. 8,632,469, which is a continuation-in-part of application No. PCT/US2007/015239, filed on Jun. 29, 2007, which is a continuation-in-part of application No. 11/063,836, filed on Feb. 23, 2005, now Pat. No. 7,818,053, and a continuation-in-part of application No. 10/782,149, filed on Feb. 19, 2004, now Pat. No. 7,454,244, said application No. 11/063,836 is a continuation-in-part of application No. 10/782,149, filed on Feb. 19, 2004, now Pat. No. 7,454,244.

(60) Provisional application No. 60/881,840, filed on Jan. 23, 2007, provisional application No. 60/817,422, filed on Jun. 30, 2006, provisional application No. 60/502,139, filed on Sep. 11, 2003, provisional application No. 60/493,145, filed on Aug. 7, 2003, provisional application No. 60/449,266, filed on Feb. 21, 2003.

(51) Int. Cl.
*A61B 5/107* (2006.01)
*A61B 17/00* (2006.01)

(56) References Cited

U.S. PATENT DOCUMENTS

| | | |
|---|---|---|
| 4,327,723 A | 5/1982 | Frankhouser |
| 4,365,639 A | 12/1982 | Goldreyer |
| 4,380,237 A | 4/1983 | Newbower |
| 4,417,886 A | 11/1983 | Frankhouser et al. |
| 4,562,843 A | 1/1986 | Djordjevich et al. |
| 4,587,975 A | 5/1986 | Salo et al. |
| 4,644,960 A | 2/1987 | Johans |
| 4,660,571 A | 4/1987 | Hess et al. |
| 4,840,182 A | 6/1989 | Carlson |
| 4,841,977 A | 6/1989 | Griffith et al. |
| 4,873,987 A | 10/1989 | Djordjevich et al. |
| 4,899,759 A | 2/1990 | Pederson et al. |
| 4,911,174 A | 3/1990 | Pederson et al. |
| 4,957,110 A | 9/1990 | Vogel et al. |
| 5,004,456 A | 4/1991 | Botterbusch et al. |
| 5,058,583 A | 10/1991 | Geddes et al. |
| 5,078,678 A | 1/1992 | Katims |
| 5,121,750 A | 6/1992 | Katims |
| 5,125,410 A | 6/1992 | Misono et al. |
| 5,174,299 A | 12/1992 | Nelson |
| 5,205,830 A | 4/1993 | Dassa et al. |
| 5,233,994 A | 8/1993 | Shmulewitz |
| 5,243,995 A | 9/1993 | Maier |
| 5,246,426 A | 9/1993 | Lewis et al. |
| 5,275,162 A | 1/1994 | Edwards et al. |
| 5,366,443 A | 11/1994 | Eggers et al. |
| 5,417,208 A | 5/1995 | Winkler |
| 5,453,576 A | 9/1995 | Krivitski |
| 5,522,880 A | 6/1996 | Barone et al. |
| 5,536,248 A | 7/1996 | Weaver et al. |
| 5,555,618 A | 9/1996 | Winkler |
| 5,599,299 A | 2/1997 | Weaver et al. |
| 5,603,333 A | 2/1997 | Konings |
| 5,634,465 A | 6/1997 | Schmiesing et al. |
| 5,665,103 A | 9/1997 | Lafontaine et al. |
| 5,702,433 A | 12/1997 | Taylor et al. |
| 5,769,786 A | 6/1998 | Wiegel |
| RE35,924 E | 10/1998 | Winkler |
| 5,827,192 A | 10/1998 | Gopakumaran et al. |
| 5,836,875 A | 11/1998 | Webster, Jr. |
| 5,842,998 A | 12/1998 | Gopakumaran et al. |
| 5,971,933 A | 10/1999 | Gopakumaran et al. |
| 6,011,988 A | 1/2000 | Lynch et al. |
| 6,080,149 A | 6/2000 | Huang et al. |
| 6,081,737 A | 6/2000 | Shah |
| 6,112,115 A | 8/2000 | Feldman et al. |
| 6,165,977 A | 12/2000 | Mochly-Rosen |
| 6,187,744 B1 | 2/2001 | Rooney |
| 6,190,370 B1 | 2/2001 | Tsui |
| 6,191,136 B1 | 2/2001 | Marban |
| 6,231,518 B1 | 5/2001 | Grabek et al. |
| 6,233,994 B1 | 5/2001 | Roy et al. |
| 6,258,035 B1 | 7/2001 | Hoeksel et al. |
| 6,270,493 B1 | 8/2001 | Lalonde et al. |
| 6,273,855 B1 | 8/2001 | Schmid et al. |
| 6,287,260 B1 | 9/2001 | Hascoet et al. |
| 6,324,416 B1 | 11/2001 | Seibert |
| 6,325,762 B1 | 12/2001 | Tjin |
| 6,354,999 B1 | 3/2002 | Dgany et al. |
| 6,360,123 B1 | 3/2002 | Kimchi et al. |
| 6,398,738 B1 | 6/2002 | Millar |
| 6,406,422 B1 | 6/2002 | Landesberg |
| 6,456,874 B1 | 9/2002 | Hafer et al. |
| 6,471,656 B1 | 10/2002 | Shalman et al. |
| 6,471,658 B1 | 10/2002 | Daniels et al. |
| 6,477,402 B1 | 11/2002 | Lynch et al. |
| 6,494,832 B1 | 12/2002 | Feldman et al. |
| 6,503,202 B1 | 1/2003 | Hossack et al. |
| 6,506,159 B2 | 1/2003 | Hascoet et al. |
| 6,511,413 B2 | 1/2003 | Landesberg |
| 6,514,226 B1 | 2/2003 | Levin et al. |
| 6,545,678 B1 | 4/2003 | Ohazama |
| 6,569,103 B2 | 5/2003 | Hoeksel et al. |
| 6,569,862 B1 | 5/2003 | Marban |
| 6,652,505 B1 | 11/2003 | Tsugita |
| 6,663,661 B2 | 12/2003 | Boneau |
| 6,666,828 B2 | 12/2003 | Greco et al. |
| 6,711,429 B1 | 3/2004 | Gilboa et al. |
| 6,799,064 B1 | 9/2004 | Hassett |
| 6,887,206 B2 | 5/2005 | Hoeksel et al. |
| 6,905,469 B2 | 6/2005 | Tascoet et al. |
| 6,922,579 B2 | 7/2005 | Taimisto et al. |
| 6,926,674 B2 | 8/2005 | Tenerz et al. |
| 6,939,313 B2 | 9/2005 | Saadat et al. |
| 6,986,744 B1 | 1/2006 | Krivitski |
| 7,065,403 B1 | 6/2006 | Mouchawar et al. |
| 7,069,072 B2 | 6/2006 | Jansen et al. |
| 7,128,734 B1 | 10/2006 | Wilson et al. |
| 7,141,019 B2 | 11/2006 | Pearlman |
| 7,169,107 B2 | 1/2007 | Jersey-Willuhn et al. |
| 7,169,109 B2 | 1/2007 | Jansen et al. |
| 7,189,205 B2 | 3/2007 | McMorrow et al. |
| 7,189,208 B1 | 3/2007 | Beatty et al. |
| 7,236,820 B2 | 6/2007 | Mabary et al. |
| 7,270,662 B2 | 9/2007 | Visram et al. |
| 7,300,430 B2 | 11/2007 | Wilson et al. |
| 7,311,702 B2 | 12/2007 | Tallarida et al. |
| 7,326,241 B2 | 2/2008 | Jang |
| 7,381,204 B2 | 6/2008 | Wilson et al. |
| 7,454,244 B2 | 11/2008 | Kassab et al. |
| 7,519,424 B2 | 4/2009 | Dennis et al. |
| 7,599,730 B2 | 10/2009 | Hunter et al. |
| 7,601,138 B2 | 10/2009 | Goebel et al. |
| 7,616,992 B2 | 11/2009 | Dennis et al. |
| 7,627,376 B2 | 12/2009 | Dennis et al. |
| 7,640,053 B2 | 12/2009 | Verin |
| 7,697,972 B2 | 4/2010 | Verard et al. |
| 7,715,925 B2 | 5/2010 | Hafer et al. |
| 7,763,196 B2 | 7/2010 | Goebel et al. |
| 7,774,055 B1 | 8/2010 | Min |
| 7,775,986 B2 | 8/2010 | Roeher et al. |
| 7,833,214 B2 | 11/2010 | Wilson et al. |
| 7,846,157 B2 | 12/2010 | Kozel |
| 7,854,740 B2 | 12/2010 | Carney |
| 7,917,193 B2 | 3/2011 | Crane |
| 7,967,782 B2 | 6/2011 | Laufer et al. |
| 8,046,052 B2 | 10/2011 | Verard et al. |
| 8,060,185 B2 | 11/2011 | Hunter et al. |
| 8,078,274 B2 | 12/2011 | Kassab |
| 8,078,279 B2 | 12/2011 | Dennis et al. |

(56) References Cited

U.S. PATENT DOCUMENTS

| | | |
|---|---|---|
| 8,082,032 B2 | 12/2011 | Kassab et al. |
| 8,099,161 B2 | 1/2012 | Kassab |
| 8,114,143 B2 | 2/2012 | Kassab et al. |
| 8,133,698 B2 | 3/2012 | Silver |
| 8,185,205 B2 | 5/2012 | Ben-David et al. |
| 8,204,582 B2 | 6/2012 | Zantos et al. |
| 8,221,402 B2 | 7/2012 | Francischelli et al. |
| 8,241,274 B2 | 8/2012 | Keogh et al. |
| 8,244,339 B2 | 8/2012 | Shen et al. |
| 8,280,477 B2 | 10/2012 | Lau et al. |
| 8,303,505 B2 | 11/2012 | Webler et al. |
| 8,326,419 B2 | 12/2012 | Rosenberg et al. |
| 8,343,096 B2 | 1/2013 | Kirschenman et al. |
| 8,374,689 B2 | 2/2013 | Gopinathan et al. |
| 8,388,541 B2 | 3/2013 | Messerly et al. |
| 8,388,546 B2 | 3/2013 | Rothenberg |
| 8,401,616 B2 | 3/2013 | Verard et al. |
| 8,409,103 B2 | 4/2013 | Grunwald et al. |
| 8,494,794 B2 | 7/2013 | Putta et al. |
| 8,521,249 B2 | 8/2013 | O'Dea |
| 8,597,193 B2 | 12/2013 | Grunwald et al. |
| 8,632,469 B2 | 1/2014 | Kassab |
| 8,798,712 B2 | 8/2014 | Gopinathan et al. |
| 8,825,151 B2 | 9/2014 | Gopinathan et al. |
| 9,006,708 B2 | 4/2015 | Bennett et al. |
| 9,066,708 B2 | 6/2015 | Kassab |
| 10,172,538 B2 | 1/2019 | Kassab |
| 10,413,211 B2 * | 9/2019 | Kassab ............... A61B 5/0538 |
| 10,524,685 B2 | 1/2020 | Kassab |
| 11,490,829 B2 * | 11/2022 | Kassab ............... A61B 5/0538 |
| 2001/0012934 A1 | 8/2001 | Chandrasekaran et al. |
| 2002/0049488 A1 | 4/2002 | Boneau |
| 2002/0087089 A1 | 7/2002 | Ben-Haim |
| 2002/0129952 A1 | 9/2002 | Matsudate et al. |
| 2002/0165537 A1 | 11/2002 | Kelley et al. |
| 2002/0177783 A1 | 11/2002 | Khalil |
| 2003/0013986 A1 | 1/2003 | Saadat |
| 2003/0130711 A1 | 7/2003 | Pearson et al. |
| 2003/0149368 A1 | 8/2003 | Hennemann et al. |
| 2003/0163128 A1 | 8/2003 | Patil et al. |
| 2003/0171894 A1 | 9/2003 | Giovanni Battista Mancini et al. |
| 2003/0195433 A1 | 10/2003 | Turovskiy et al. |
| 2004/0019447 A1 | 1/2004 | Shachar |
| 2004/0024329 A1 | 2/2004 | Jansen et al. |
| 2004/0116816 A1 | 6/2004 | Tenerz et al. |
| 2004/0122421 A1 | 6/2004 | Wood |
| 2004/0167426 A1 | 8/2004 | Vantrappen |
| 2004/0220562 A1 | 11/2004 | Garabedian et al. |
| 2004/0230131 A1 * | 11/2004 | Kassab ............... A61B 5/036 600/587 |
| 2004/0243116 A1 | 12/2004 | Joye et al. |
| 2004/0254495 A1 | 12/2004 | Mabary et al. |
| 2005/0010110 A1 | 1/2005 | Black et al. |
| 2005/0096647 A1 | 5/2005 | Steinke et al. |
| 2005/0119647 A1 | 6/2005 | He et al. |
| 2005/0119660 A1 | 6/2005 | Bourlion et al. |
| 2005/0203434 A1 * | 9/2005 | Kassab ............... A61B 5/0215 600/547 |
| 2005/0240147 A1 | 10/2005 | Makower et al. |
| 2005/0256521 A1 | 11/2005 | Kozel |
| 2006/0009759 A1 | 1/2006 | Christian et al. |
| 2006/0116633 A1 | 6/2006 | Shachar |
| 2006/0149166 A1 | 7/2006 | Zvuloni |
| 2006/0173251 A1 | 8/2006 | Govari et al. |
| 2006/0206106 A1 | 9/2006 | Scholl et al. |
| 2007/0016007 A1 | 1/2007 | Govari et al. |
| 2007/0016069 A1 | 1/2007 | Grunwald et al. |
| 2007/0016070 A1 | 1/2007 | Grunwald et al. |
| 2007/0016072 A1 | 1/2007 | Grunwald et al. |
| 2007/0062547 A1 | 3/2007 | Pappone |
| 2007/0083194 A1 | 4/2007 | Kunis et al. |
| 2007/0161914 A1 | 7/2007 | Zdeblick et al. |
| 2007/0232896 A1 | 10/2007 | Gilboa et al. |
| 2007/0255162 A1 * | 11/2007 | Abboud ............... A61B 5/0537 600/547 |
| 2007/0255270 A1 | 11/2007 | Carney |
| 2008/0004652 A1 | 1/2008 | Abboud et al. |
| 2008/0033316 A1 | 2/2008 | Kassab et al. |
| 2008/0033350 A1 | 2/2008 | Wilson et al. |
| 2008/0176271 A1 | 7/2008 | Silver et al. |
| 2008/0188830 A1 | 8/2008 | Rosenblatt et al. |
| 2008/0190438 A1 | 8/2008 | Harlev et al. |
| 2008/0194996 A1 | 8/2008 | Kassab |
| 2008/0255475 A1 | 10/2008 | Kondrosky et al. |
| 2008/0269581 A1 | 10/2008 | Wood et al. |
| 2008/0269611 A1 | 10/2008 | Pedrizzetti et al. |
| 2008/0294041 A1 | 11/2008 | Kassab |
| 2008/0319350 A1 | 12/2008 | Wallace et al. |
| 2009/0005674 A1 | 1/2009 | Saadat et al. |
| 2009/0005675 A1 | 1/2009 | Grunwald et al. |
| 2009/0062664 A1 | 3/2009 | Chang et al. |
| 2009/0062684 A1 | 3/2009 | Gregersen et al. |
| 2009/0118612 A1 | 5/2009 | Grunwald et al. |
| 2009/0118637 A1 | 5/2009 | Kassab et al. |
| 2009/0143640 A1 | 6/2009 | Saadat et al. |
| 2009/0156926 A1 | 6/2009 | Messerly et al. |
| 2009/0177090 A1 | 7/2009 | Grunwald et al. |
| 2009/0182287 A1 | 7/2009 | Kassab |
| 2009/0209872 A1 | 8/2009 | Pop |
| 2009/0209950 A1 | 8/2009 | Starksen |
| 2009/0216133 A1 | 8/2009 | Kassab |
| 2009/0259124 A1 | 10/2009 | Rothenberg |
| 2009/0262982 A1 | 10/2009 | Markowitz et al. |
| 2009/0262992 A1 | 10/2009 | Markowitz et al. |
| 2009/0264778 A1 | 10/2009 | Markowitz et al. |
| 2009/0270729 A1 | 10/2009 | Corbucci et al. |
| 2009/0270746 A1 | 10/2009 | Min |
| 2010/0010355 A1 | 1/2010 | Kassab |
| 2010/0010488 A1 | 1/2010 | Kassab et al. |
| 2010/0010612 A1 | 1/2010 | Gelbart et al. |
| 2010/0036227 A1 | 2/2010 | Cox et al. |
| 2010/0041984 A1 | 2/2010 | Shapland et al. |
| 2010/0049062 A1 | 2/2010 | Ziv |
| 2010/0076328 A1 | 3/2010 | Matsumura et al. |
| 2010/0198346 A1 | 8/2010 | Keogh et al. |
| 2010/0210938 A1 | 8/2010 | Verard et al. |
| 2010/0222786 A1 | 9/2010 | Kassab |
| 2010/0268059 A1 | 10/2010 | Ryu et al. |
| 2010/0291521 A1 | 11/2010 | Simon |
| 2011/0015533 A1 | 1/2011 | Cox et al. |
| 2011/0034823 A1 | 2/2011 | Gelbart et al. |
| 2011/0196255 A1 | 8/2011 | Kassab |
| 2011/0245662 A1 | 10/2011 | Eggers et al. |
| 2011/0270237 A1 | 11/2011 | Werneth et al. |
| 2011/0306867 A1 | 12/2011 | Gopinathan et al. |
| 2012/0053441 A1 | 3/2012 | Kassab |
| 2012/0059249 A1 | 3/2012 | Verard et al. |
| 2012/0071782 A1 | 3/2012 | Patil et al. |
| 2012/0078342 A1 | 3/2012 | Vollkron et al. |
| 2012/0108950 A1 | 5/2012 | He et al. |
| 2012/0136242 A1 | 5/2012 | Qi et al. |
| 2012/0143029 A1 | 6/2012 | Silverstein et al. |
| 2012/0143078 A1 | 6/2012 | Kassab et al. |
| 2012/0169712 A1 | 7/2012 | Hill et al. |
| 2012/0172746 A1 | 7/2012 | Kassab |
| 2012/0226148 A1 | 9/2012 | Jaggi et al. |
| 2012/0302869 A1 | 11/2012 | Koyrakh et al. |
| 2013/0041269 A1 | 2/2013 | Stahmann et al. |
| 2013/0267835 A1 | 10/2013 | Edwards |
| 2013/0338468 A1 | 12/2013 | Kassab |
| 2014/0066738 A1 | 3/2014 | Kassab |
| 2014/0275913 A1 | 9/2014 | Hill et al. |
| 2015/0080762 A1 | 3/2015 | Kassab et al. |
| 2015/0272451 A1 | 10/2015 | Razavi et al. |
| 2015/0297113 A1 | 10/2015 | Kassab et al. |
| 2016/0067464 A1 | 3/2016 | Kim et al. |
| 2016/0081585 A1 | 3/2016 | Halter |
| 2017/0071501 A1 | 3/2017 | Kassab |
| 2017/0347896 A1 | 12/2017 | Keyes et al. |
| 2019/0110844 A1 | 4/2019 | Misener et al. |
| 2019/0133489 A1 | 5/2019 | Kassab |
| 2020/0069217 A1 | 3/2020 | Kassab |
| 2021/0093757 A1 | 4/2021 | Turer et al. |
| 2022/0151709 A1 | 5/2022 | Misener et al. |

(56) References Cited

U.S. PATENT DOCUMENTS

| | | |
|---|---|---|
| 2022/0401702 A1 | 12/2022 | Misener et al. |
| 2023/0011437 A1 | 1/2023 | Sowards et al. |
| 2024/0041533 A1 | 2/2024 | Misener et al. |

FOREIGN PATENT DOCUMENTS

| | | |
|---|---|---|
| EP | 0596344 A1 | 5/1994 |
| EP | 0786266 A1 | 7/1997 |
| EP | 0988827 A1 | 3/2000 |
| EP | 1025805 A1 | 8/2000 |
| EP | 2061532 A1 | 5/2009 |
| EP | 2134403 A2 | 12/2009 |
| WO | 1998035611 A1 | 8/1998 |
| WO | 2002019905 A1 | 3/2002 |
| WO | 2002085442 A1 | 10/2002 |
| WO | 2003092495 A1 | 11/2003 |
| WO | 2004004828 A2 | 1/2004 |
| WO | 2004075928 A2 | 9/2004 |
| WO | 2006005985 A1 | 1/2006 |
| WO | 2007015239 A2 | 2/2007 |
| WO | 2008000833 A1 | 1/2008 |
| WO | 2008031821 A1 | 3/2008 |
| WO | 2008126074 A2 | 10/2008 |
| WO | 2009003138 A1 | 12/2008 |
| WO | 2009/019707 A1 | 2/2009 |
| WO | 2009/142918 A2 | 11/2009 |
| WO | 2010/124169 A1 | 10/2010 |
| WO | 2010130723 A1 | 11/2010 |
| WO | 2011023911 A1 | 3/2011 |
| WO | 2011024961 A1 | 3/2011 |
| WO | 2011026337 A1 | 3/2011 |
| WO | 2012/114219 A1 | 8/2012 |
| WO | 2012110955 A1 | 8/2012 |
| WO | 2012173697 A1 | 12/2012 |
| WO | 2013/152335 A1 | 10/2013 |
| WO | 2016/040394 A1 | 3/2016 |
| WO | 2019/117943 A1 | 6/2019 |
| WO | 2022266501 A1 | 12/2022 |
| WO | 2023283199 A1 | 1/2023 |

OTHER PUBLICATIONS

AU 2013243252 filed Aug. 13, 2014 Notice of Acceptance dated Mar. 23, 2017.
CA 2864860 filed Aug. 15, 2014 Office Action dated Jan. 30, 2019.
CN 201380018999.6 filed Oct. 8, 2014 First Office Action dated Feb. 14, 2016.
CN 201380018999.6 filed Oct. 8, 2014 Office Action dated Aug. 30, 2016.
CN 201380018999.6 filed Oct. 8, 2014 Office Action dated Mar. 30, 2017.
CO 14.244.362 filed Nov. 5, 2016 Office Action dated Jan. 23, 2017.
CO 14.244.362 filed Nov. 5, 2016 Office Action dated Nov. 7, 2016.
CO 14244362 filed Nov. 5, 2016 Office Action dated Feb. 5, 2018.
Douglas A. Hettrick, et al. "Finite Element Model Determination of . . . " Annals of Biomedical Engineering. vol. 27, pp. 151-159, 1999.
Douglas A. Hettrick, et al. "In Vivo Measurement of Real-Time Aortic Segmental Volume . . . " Annals of Biomedical Engineering. vol. 26, pp. 431-440, 1998.
EP 13772981.0 filed Apr. 5, 2013 Extended European Search Report dated Oct. 14, 2015.
Hoekstein and Inbar, "Cardiac Stroke vol. Estimation . . . "Technion Department of Electrical Engineering Publication EE Pub No. 991, Feb. 1994.
International Searching Authority, International Preliminary Report on Patentability, PCT/US1 0/32178, dated Nov. 3, 2011.
International Searching Authority, PCT Search Report and Written Opinion, PCT/US04/04828, dated Jul. 6, 2005.
International Searching Authority, PCT Search Report and Written Opinion, PCT/US06/05985, dated Aug. 8, 2007.
International Searching Authority, PCT Search Report and Written Opinion, PCT/US11/23911, dated Apr. 4, 2011.
International Searching Authority, PCT Search Report and Written Opinion, PCT/US11/24961, dated Aug. 30, 2012.
International Searching Authority, PCT Search Report and Written Opinion, PCT/US11/26337, dated Sep. 7, 2012.
Konings, M. K. et al. "Correct positioning of central venous catheters using a new electric method," J Vasc Access Mar. 9, 2015; 16 (4): 327-332.
L. Kornet, et al. "Conductance Method for the Measurement of . . . " Annals of Biomedical Engineering, vol. 27. pp. 141-150, 1999.
MX/a/2014/011884 filed Oct. 1, 2014 Office Action dated Feb. 20, 2018.
MX/a/2014/011884 filed Oct. 1, 2014 Office Action dated Jan. 30, 2017.
MX/a/2014/011884 filed Oct. 1, 2014 Office Action dated Oct. 3, 2017.
PCT/US07/15239 filed Jun. 29, 2007 International Search Report dated Jun. 5, 2008.
PCT/US2008/000833 filed Jan. 23, 2008 International Search Report dated Nov. 6, 2008.
PCT/US2013/035527 filed Apr. 5, 2013 International Preliminary Report on Patentability dated Oct. 16, 2014.
PCT/US2015/049043 filed Sep. 8, 2015 International Search Report and Written Opinion dated Feb. 1, 2016.
PCT/US2022/034088 filed Jun. 17, 2022 International Search Report and Written Opinion dated Oct. 7, 2022.
Supplementary European Search Report for EP Application Serial No. 04 71 2383 to Electro-Cat, LLC, dated Aug. 6, 2007.
Svendsen, Mark C. et al., "Accurate nonfluoroscopic guidance and tip location of peripherally inserted central catheters using a conductance guidewire system," Journal of Vascular Surgery: Venous and Lymphatic Disorders, vol. 1, Issue 2, pp. 202-208. (Jan. 5, 2013).
U.S. Appl. No. 14/010,139, filed Aug. 26, 2013 Advisory Action dated Oct. 29, 2015.
U.S. Appl. No. 14/010,139, filed Aug. 26, 2013 Final Office Action dated Aug. 20, 2015.
U.S. Appl. No. 14/010,139, filed Aug. 26, 2013 Non-Final Office Action dated Dec. 15, 2015.
U.S. Appl. No. 14/010,139, filed Aug. 26, 2013 Non-Final Office Action dated Mar. 26, 2015.
U.S. Appl. No. 14/010,139, filed Aug. 26, 2013 Notice of Allowance dated May 20, 2016.
U.S. Appl. No. 14/010,169, filed Aug. 26, 2013 Advisory Action dated Jan. 17, 2018.
U.S. Appl. No. 14/010,169, filed Aug. 26, 2013 Advisory Action dated Jan. 25, 2017.
U.S. Appl. No. 14/010,169, filed Aug. 26, 2013 Advisory Action dated Jun. 7, 2016.
U.S. Appl. No. 14/010,169, filed Aug. 26, 2013 Final Office Action dated Mar. 22, 2016.
U.S. Appl. No. 14/010,169, filed Aug. 26, 2013 Final Office Action dated Nov. 17, 2016.
U.S. Appl. No. 14/010,169, filed Aug. 26, 2013 Final Office Action dated Oct. 30, 2017.
U.S. Appl. No. 14/010,169, filed Aug. 26, 2013 Non-Final Action dated Feb. 28, 2018.
U.S. Appl. No. 14/010,169, filed Aug. 26, 2013 Non-Final Office Action dated Aug. 18, 2016.
U.S. Appl. No. 14/010,169, filed Aug. 26, 2013 Non-Final Office Action dated Dec. 7, 2015.
U.S. Appl. No. 14/010,169, filed Aug. 26, 2013 Non-Final Office Action dated Jul. 7, 2017.
U.S. Appl. No. 14/010,202, filed Aug. 26, 2013 Advisory Action dated Jun. 20, 2017.
U.S. Appl. No. 14/010,202, filed Aug. 26, 2013 Advisory Action dated Nov. 28, 2018.
U.S. Appl. No. 14/010,202, filed Aug. 26, 2013 Advisory Action dated Oct. 12, 2016.
U.S. Appl. No. 14/010,202, filed Aug. 26, 2013 Final Office Action dated Jul. 26, 2016.

(56) References Cited

OTHER PUBLICATIONS

U.S. Appl. No. 14/010,202, filed Aug. 26, 2013 Final Office Action dated Mar. 29, 2017.
U.S. Appl. No. 14/010,202, filed Aug. 26, 2013 Non-Final Office Action dated Apr. 15, 2016.
U.S. Appl. No. 14/010,202, filed Aug. 26, 2013 Non-Final Office Action dated Dec. 15, 2016.
U.S. Appl. No. 14/010,202, filed Aug. 26, 2013 Non-Final Office Action dated Dec. 29, 2017.
U.S. Appl. No. 14/010,202, filed Aug. 26, 2013 Non-Final Office Action dated Jan. 13, 2016.
U.S. Appl. No. 14/010,202, filed Aug. 26, 2013 Notice of Allowance dated May 15, 2019.
U.S. Appl. No. 14/394,204, filed Oct. 13, 2014 Advisory Action dated Jul. 24, 2018.
U.S. Appl. No. 14/394,204, filed Oct. 13, 2014 Advisory Action dated Oct. 31, 2016.
U.S. Appl. No. 14/394,204, filed Oct. 13, 2014 Advisory Action dated Sep. 13, 2017.
U.S. Appl. No. 14/394,204, filed Oct. 13, 2014 Examiner's Answer dated Dec. 12, 2019.
U.S. Appl. No. 14/394,204, filed Oct. 13, 2014 Final Action dated May 8, 2018.
U.S. Appl. No. 14/394,204, filed Oct. 13, 2014 Final Office Action dated Apr. 15, 2019.
U.S. Appl. No. 14/394,204, filed Oct. 13, 2014 Final Office Action dated Aug. 16, 2016.
U.S. Appl. No. 14/394,204, filed Oct. 13, 2014 Final Office Action dated Jun. 21, 2017.
U.S. Appl. No. 14/394,204, filed Oct. 13, 2014 Non-Final Action dated Dec. 11, 2017.
U.S. Appl. No. 14/394,204, filed Oct. 13, 2014 Non-Final Office Action dated Dec. 22, 2016.
U.S. Appl. No. 14/394,204, filed Oct. 13, 2014 Non-Final Office Action dated Feb. 24, 2016.
U.S. Appl. No. 14/394,204, filed Oct. 13, 2014 Non-Final Office Action dated Nov. 20, 2018.
U.S. Appl. No. 14/394,204, filed Oct. 13, 2014 Notice of Allowance dated Jan. 22, 2021.
U.S. Appl. No. 14/394,204, filed Oct. 13, 2014 Patent Board Decision dated Nov. 3, 2020.
U.S. Appl. No. 14/752,697, filed Jun. 26, 2015 Advisory Action dated Oct. 6, 2017.
U.S. Appl. No. 14/752,697, filed Jun. 26, 2015 Advisory Action dated Oct. 9, 2018.
U.S. Appl. No. 14/752,697, filed Jun. 26, 2015 Examiner's Answer dated Apr. 17, 2020.
U.S. Appl. No. 14/752,697, filed Jun. 26, 2015 Final Office Action dated Jul. 21, 2017.
U.S. Appl. No. 14/752,697, filed Jun. 26, 2015 Final Office Action dated Jul. 24, 2018.
U.S. Appl. No. 14/752,697, filed Jun. 26, 2015 Final Office Action dated Sep. 11, 2019.
U.S. Appl. No. 14/752,697, filed Jun. 26, 2015 Non-Final Office Action dated Feb. 7, 2017.
U.S. Appl. No. 14/752,697, filed Jun. 26, 2015 Non-Final Office Action dated Jan. 31, 2018.
U.S. Appl. No. 14/752,697, filed Jun. 26, 2015 Non-Final Office Action dated Mar. 12, 2019.
U.S. Appl. No. 14/752,697, filed Jun. 26, 2015 Notice of Allowance dated Jul. 26, 2021.
U.S. Appl. No. 14/752,697, filed Jun. 26, 2015 Patent Board Decision dated May 3, 2021.
U.S. Appl. No. 14/848,331, filed Sep. 8, 2015 Non-Final Office Action dated Feb. 6, 2018.
U.S. Appl. No. 14/848,331, filed Sep. 8, 2015 Notice of Allowance dated Aug. 1, 2018.
U.S. Appl. No. 14/848,331, filed Sep. 8, 2015 Restriction Requirement dated Nov. 22, 2017.
U.S. Appl. No. 15/269,767, filed Sep. 19, 2016 Non-Final Office Action dated Mar. 13, 2019.
U.S. Appl. No. 15/269,767, filed Sep. 19, 2016 Notice of Allowance dated Aug. 30, 2019.
U.S. Appl. No. 16/219,806, filed Dec. 13, 2018 Non-Final Office Action dated May 4, 2021.
U.S. Appl. No. 16/241,730, filed Jan. 7, 2019 Final Office Action dated Mar. 7, 2022.
U.S. Appl. No. 16/241,730, filed Jan. 7, 2019 Non-Final Office Action dated Nov. 18, 2021.
U.S. Appl. No. 16/241,730, filed Jan. 7, 2019 Notice of Allowance dated Aug. 15, 2022.
U.S. Appl. No. 16/565,161, filed Sep. 9, 2019 Non-Final Office Action dated Mar. 17, 2022.
U.S. Appl. No. 16/565,161, filed Sep. 9, 2019 Notice of Allowance dated Jul. 5, 2022.
PCT/US2022/036142 filed Jul. 5, 2022 International Search Report and Written Opinion dated Nov. 14, 2022.
U.S. Appl. No. 17/534,239, filed Nov. 23, 2021 Notice of Allowance dated Jun. 15, 2023.
U.S. Appl. No. 17/534,239, filed Nov. 23, 2021 Notice of Allowance dated May 31, 2023.

\* cited by examiner

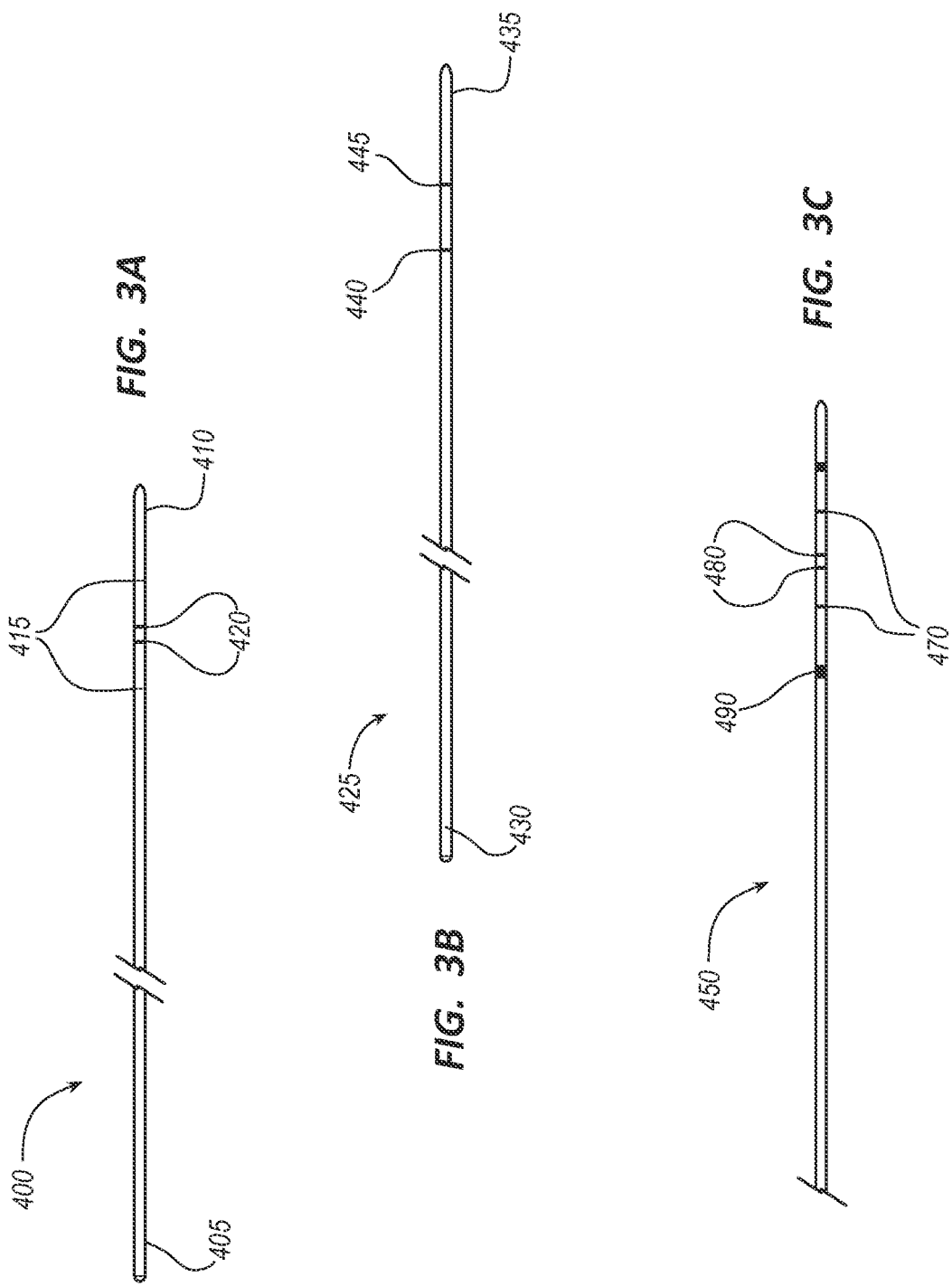

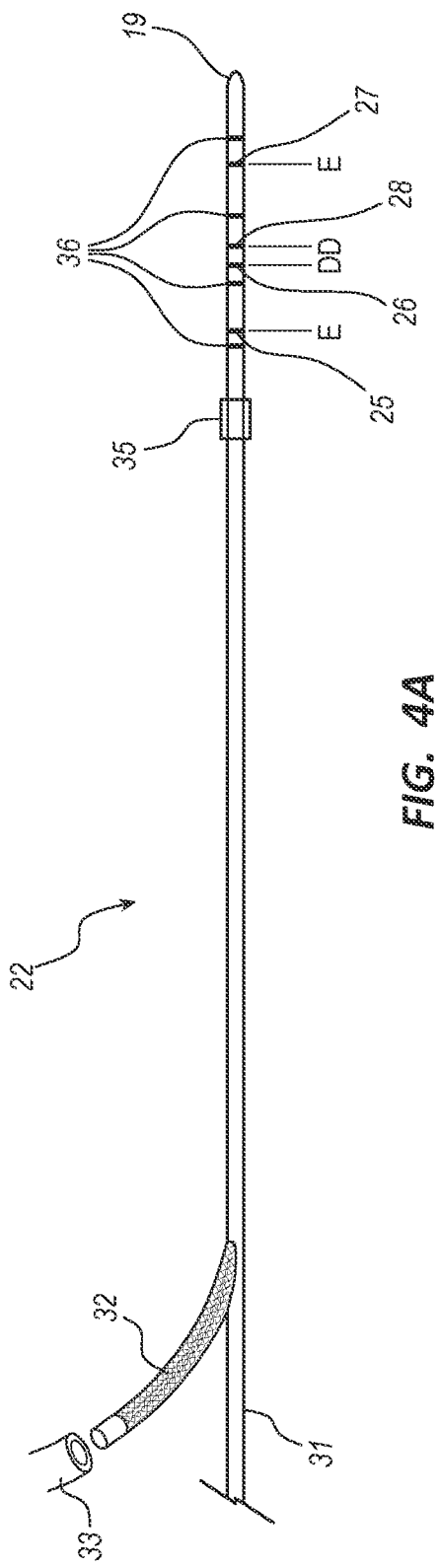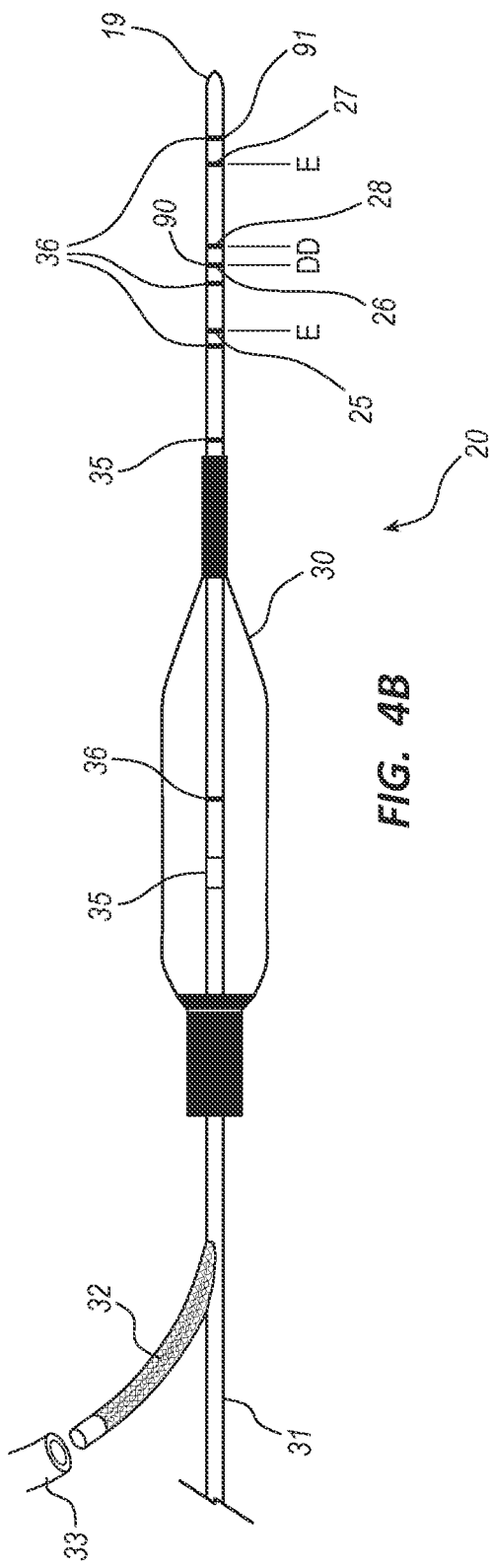
FIG. 4A
FIG. 4B

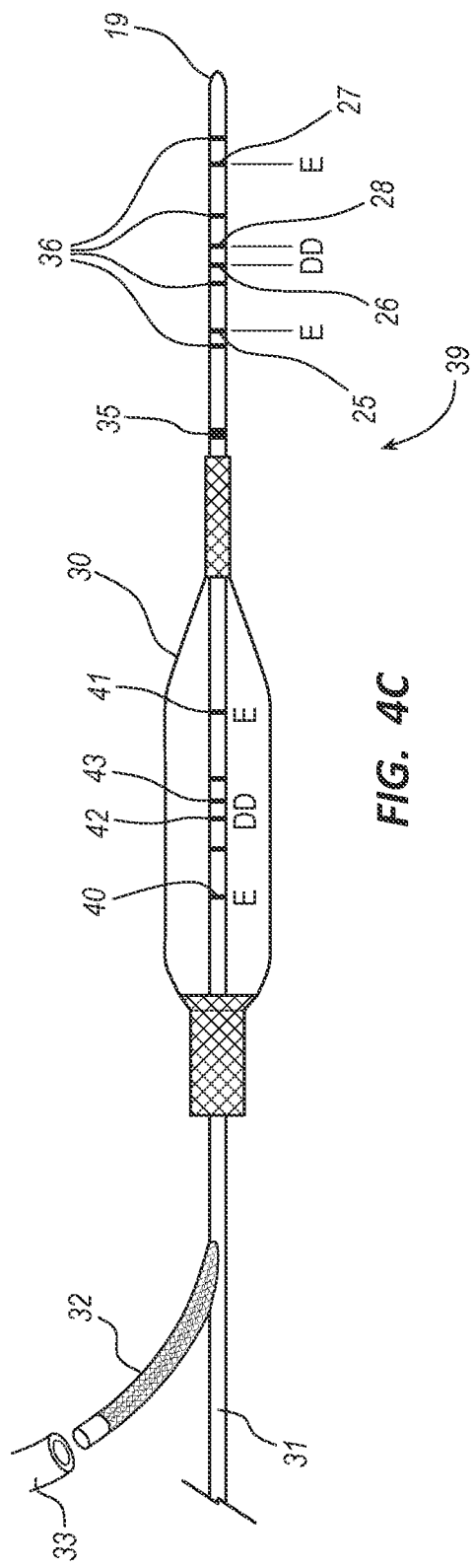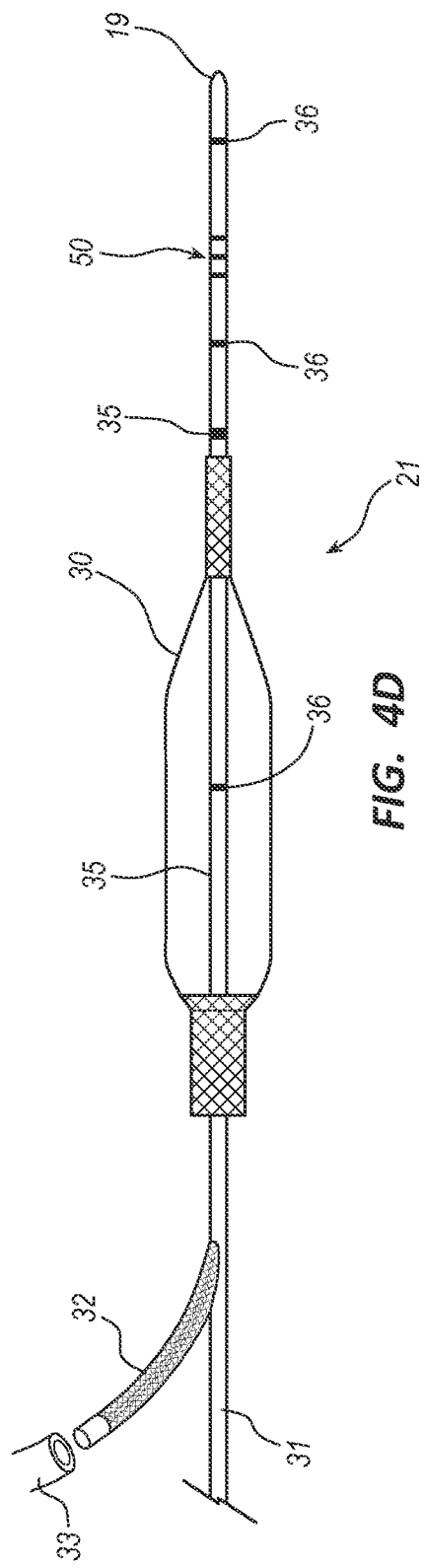
FIG. 4C
FIG. 4D envelope data, peak-peak, of voltage at the detection electrodes

SYSTEMS, DEVICES, AND METHODS FOR MAPPING ORGAN PROFILES

PRIORITY

This application is a continuation of U.S. patent application Ser. No. 16/565,161, filed Sep. 9, 2019, now U.S. Pat. No. 11,490,829, which is a continuation of U.S. patent application Ser. No. 14/010,202, filed Aug. 26, 2013, now U.S. Pat. No. 10,413,211, which is a continuation of U.S. patent application Ser. No. 12/522,432, now U.S. Pat. No. 8,632,469, which is a § 371 application of International Patent Application No. PCT/US2008/000833, filed Jan. 23, 2008, which claims the priority benefit of U.S. Provisional Application No. 60/881,840, filed Jan. 23, 2007, and which is a continuation-in-part of International Patent Application No. PCT/US2007/015239, filed Jun. 29, 2007, which claims the priority benefit of U.S. Provisional Application No. 60/817,422, filed Jun. 30, 2006, and which is a continuation-in-part of: (1) U.S. patent application Ser. No. 10/782,149, filed Feb. 19, 2004, now U.S. Pat. No. 7,454,244 which claims the benefit of priority to: (a) U.S. Provisional Application No. 60/449,266, filed Feb. 21, 2003, (b) U.S. Provisional Application No. 60/493,145, filed Aug. 7, 2003, and (c) U.S. Provisional Application No. 60/502,139, filed Sep. 11, 2003; and (2) U.S. patent application Ser. No. 11/063,836, filed Feb. 23, 2005, now U.S. Pat. No. 7,818,053, which is a continuation-in-part of U.S. patent application Ser. No. 10/782,149, filed Feb. 19, 2004, now U.S. Pat. No. 7,454,244. Each of the foregoing applications is hereby incorporated by reference in its entirety into this application.

BACKGROUND

Treatment of certain cardiovascular diseases such as aortic aneurysms or chronic heart failure often includes positioning devices within the aorta or the coronary sinus through catheterization. Such procedures require precise placement of the implanted devices within the target lumens, and can result in severe complications if such implantations are inaccurate. Accordingly, having a clear map of the aorta and/or coronary sinus minimizes the risks involved in these procedures.

An aortic aneurysm is a ballooning of the wall of an artery resulting from the weakening of the artery due to disease, heredity, aging or other conditions. When an area of the aortic wall weakens, the pressure of the blood flowing through the weakened area causes the vessel wall to balloon out, forming a blood-filled aneurysm sack. Although most aneurysms are initially small, aneurysms tend to enlarge over time. Left untreated, the aneurysm will frequently rupture, resulting in loss of blood through the rupture.

Aortic aneurysms are the most common form of arterial aneurysm and are life threatening due to the massive internal bleeding that results from rupture. In the past 30 years, the occurrence of abdominal aortic aneurysms ("AAA"), in particular, has increased threefold. According to the Society of Vascular Surgeons, ruptured aneurysms account for more than 15,000 American deaths each year, making the AAA the thirteenth leading cause of death in the United States.

The aorta is the main artery that carries blood from the heart to the rest of the body. The aorta arises from the left ventricle of the heart, extending upward and bending over behind the heart, and thereafter extending downward through the thorax and abdomen. The abdominal aorta supplies the two side vessels to the kidneys, the renal arteries. Below the level of the renal arteries, the abdominal aorta continues to about the level of the fourth lumbar vertebrae where it divides into the iliac arteries. The iliac arteries supply blood to the lower extremities and perineal region. Accordingly, the aorta is a major arterial component of the circulatory system and maintaining its general condition is critical to the overall health of the patient.

AAA is the most common type of aortic aneurysm. Specifically, AAA is an aneurysm that occurs in the portion of the abdominal aorta that is particularly susceptible to weakening between the renal arteries and the iliac arteries. While, in other areas of the aorta the indication that intervention is necessary is when the aneurysm reaches about 5 cm in diameter, an aortic aneurysm larger than about 4 cm in diameter in this section of the aorta is ominous. Left untreated, the AAA may rupture, resulting in rapid and usually fatal hemorrhaging.

Although the mortality rate for an aortic aneurysm is extremely high (about 75-80%), there is also considerable mortality and morbidity associated with surgical intervention to repair an aortic aneurysm. This intervention typically involves going through the abdominal wall to the location of the aneurysm in order to bypass or replace the diseased section of the aorta. A prosthetic device, typically a synthetic tube, is often used for this purpose. The graft serves to exclude the aneurysm from the circulatory system, thus relieving the pressure and stress on the weakened section of the aorta at the aneurysm.

Repair of an aortic aneurysm by surgical means is a major operative procedure. In addition, substantial morbidity accompanies the procedure, resulting in a protracted recovery period. Finally, the procedure entails a substantial risk of mortality. While surgical intervention may be required in spite of these risks, certain patients may not be able to tolerate the stress of intra-abdominal surgery. It is desirable to reduce the mortality and morbidity associated with intra-abdominal surgical intervention.

In recent years, methods have been developed to attempt to treat an aortic aneurysm without the attendant risks of surgical intervention. One such minimally invasive alternative is endovascular aneurysm repair ("EVAR"). EVAR treatment involves the placement of an endovascular stent in the aneurismal area of the aorta through a percutaneous technique. Specifically, in most circumstances, the endovascular stent is inserted into a blood vessel (artery or vein), usually through an entry site located in the upper leg or neck. Under fluoroscopy, the stent is navigated through the blood vessels until it reaches the aorta where it is positioned over the aneurysm.

While EVAR has been reported to have a lower mortality rate as compared to open surgical repair, to effectuate a successful delivery of EVAR, it is necessary to have a clear map of the aorta such that the stent can be properly positioned. Although the aneurysmic regions of the aorta may be quite diseased and atherosclerotic, for the procedure to be successful a healthy portion of the aorta must be present to serve as a landing zone for the stent. For example, securing the stent to a diseased region of the aorta will result in a faulty seal that will not adequately reroute the blood flow away from the aneurysmic region, thereby resulting in a reoccurrence of the condition. As accurate placement of the stent is critical, visualization of the aortic structure has been an obstacle for proper navigation during delivery of the stent. Currently, clinicians perform magnetic resonance imaging prior to delivering the stent in order to supply an axial profile of the aorta. However, magnetic resonance imaging is expensive and time consuming to obtain, and the results exhibit limited spatial resolution.

Chronic heart failure ("CHF") is another cardiovascular disease, the treatment of which often includes catheterization. CHF is a disease condition in which the heart fails to function efficiently as a pump and cannot provide sufficient blood flow and/or pressure to satisfy the normal circulatory needs of a patient. A patient with acute CHF often experiences sudden shortness of breath, fainting, and irregular heartbeats that require frequent emergency room treatments. In its chronic form, CHF leads to repeated hospital stays, a deterioration in quality of life, and significant costs to the healthcare system.

In about 30% of CHF patients, the disease process compromises the myocardium's ability to contract, which thereby alters the conduction pathways through the heart. A healthy heart has specialized conduction pathways in both the atria and the ventricles that enable the rapid conduction of excitation (i.e. depolarization) throughout the myocardium. Normally, the sinoatrial node ("SA node") initiates each heart-beat cycle by depolarizing so as to generate an action potential. This action potential propagates relatively quickly through the atria, which react by contracting, and then relatively slowly through the atrio-ventricular node ("AV node"). From the AV node, activation propagates rapidly through the His-Purkinje system to the ventricles, which also react by contracting. This natural propagation synchronizes the contractions of the muscle fibers of each chamber and synchronizes the contraction of each atrium or ventricle with the contralateral atrium or ventricle.

When a patient exhibits damage to the electrical system of the heart, as is often seen in patients with CHF, severe issues may arise. Disruption of the conductance pathways through the heart can cause a delay in the beginning of right or left ventricular systole and thereby induce asynchronous atrial and ventricular activation. Electrocardiographically, this dysynchrony is manifested as a long QRS interval. Alterations in ventricular contractility frequently compromise the ability of the failing heart to eject blood and may consequently increase the severity of the regurgitant flow through the mitral valve. In patients exhibiting these severe symptoms, the intraventricular conduction delays lead to clinical instability associated with a greatly increased risk of death.

Since 2001, approximately 271,000 heart failure patients in the United States have received cardiac resynchronization therapy ("CRT") to treat moderate to severe heart failure ("HF"). Conventional CRT methods employ a pacemaker to pace both ventricles of the heart such that the heart can resynchronize. CRT devices have three leads; the first positioned in the atrium, the second positioned in the right ventricle, and the third inserted through the coronary sinus to pace the left ventricle.

Due to the required placement of the third lead, the implantation and maintenance of a CRT device are associated with a greater risk than the implantation and maintenance of a standard pacemaker device. Primarily, it is a difficult procedure to advance the pacing lead into the coronary sinus and cardiac veins and, thus, implantation fails in approximately 8% of patients. Further, in approximately 6% of patients, implantation is compromised by dissection or perforation of the coronary sinus or cardiac vein. Severe complications are associated with the inaccurate implantation of a pacing lead, including complete heart block, hemopericardium, and cardiac arrest (which, together, occurred in about 1.2% of patients).

As accurate placement of the leads is critical, the ability to visualize a map or profile of the coronary sinus is important to ensure proper navigation. Conventionally, clinicians use cardiac angiography to visualize the lumen of the blood vessels and the heart chambers. Cardiac angiography typically involves using a combination of injections of radiocontrast agent or dye and x-ray fluoroscopy to visualize the position and size of blood vessels within the heart. This process, however, is not particularly accurate and does not provide a detailed profile of the coronary sinus.

Thus, there is a need for an efficient, accurate, easy to use, and reasonably priced technique for determining the longitudinal profile of the aorta and the coronary sinus.

BRIEF SUMMARY

Various embodiments of devices, systems, and methods for localization of, body lumen junctures are disclosed herein. At least some of the disclosed embodiments allow a clinician to identify desired anatomical structures with a higher spatial resolution than with conventional techniques. For example, in certain embodiments, a clinician may use embodiments of the devices, systems and methods disclosed herein to accurately identify various bifurcations branching off of the coronary sinus. A clinician may further use the embodiments described herein to accurately place a lead within a coronary sinus or a bifurcation branching therefrom. In certain other embodiments, a clinician may use embodiments of the devices, systems and methods disclosed herein to create a conductance profile of an aorta that is capable of showing the locations of lesions or other structures. In this manner, conductance profile can be used to accurately treat an aortic aneurysm by employing a stent.

Some embodiments disclosed herein include systems for localizing a body lumen junction or other intraluminal structure. These systems comprise a catheter having a proximal end and a distal end for placement into a body lumen. The catheter may comprise a first electrode and a second electrode, and each of the first and second electrodes have a proximal end and a distal end; the distal ends of the first and second electrodes are located between the proximal and distal ends of the catheter. In some embodiments, the catheter may comprise a thin wire. The system further comprises a processor connected to the first and second electrodes of the catheter. The processor is capable of collecting conductance data to determine a profile of the body lumen. The conductance data is collected at a plurality of locations within the body lumen and determined at each of the plurality of locations when the distal ends of the first and second electrodes are immersed in a fluid within the body lumen. In some embodiments, the processor is also capable of calculating a cross-sectional area of the body lumen at each of the plurality of locations within the body lumen using the conductance data.

For certain embodiments of such systems, the relevant body lumen comprises at least a portion of an atrium, coronary sinus, aorta, a pulmonary vein-atrial junction, a blood vessel, a biliary tract, or an esophagus. Indeed, many embodiments may be used in connection with any other body lumen that is suitable for access and localization.

The body lumen may have at least some fluid inside, and the fluid may comprise blood or another suitable fluid, such as a solution of NaCl having a known conductivity. Certain embodiments of the catheter have a passageway for passing fluid through the catheter to the location of the distal ends of the first and second electrodes, such that the fluid passing through the passageway comes in contact with the distal ends of the first and second electrodes. For some embodiments, the conductance data is determined at each of a plurality of locations within the lumen when the distal ends of the first and second electrodes are immersed in a first fluid having a first conductivity and then a second fluid having a second conductivity. The conductance data may comprise a first conductance value determined at each of the plurality of locations when the distal ends of the first and second electrodes are immersed in the first fluid and a second conductance value determined at each of the plurality of locations when the distal ends of the first and second electrodes are immersed in the second fluid. The profile of the body lumen is therefore determined from the first and second conductance values collected from each of the plurality of locations, the first conductivity of the first fluid, and the second conductivity of the second fluid. The profile may consist of actual or relative values for cross-sectional areas or conductances.

Many embodiments disclosed herein have a catheter with at least four electrodes, including at least two excitation electrodes and at least two detection electrodes. Further, in certain embodiments, the catheter may comprise a thin wire having at least four electrodes. Each of the electrodes has a proximal end and a distal end, wherein the proximal ends of the electrodes may be connected to the processor directly or indirectly. In at least some embodiments, the distal ends of the excitation electrodes are located between the proximal and distal ends of the catheter, and the distal ends of the detection electrodes are located between the distal ends of the excitation electrodes.

Certain embodiments disclosed herein include a number of steps for localizing a junction or other structure within a body lumen, including providing an embodiment of a system as disclosed herein; introducing the catheter into the body lumen; providing electrical current flow to the body lumen through the catheter; measuring a first conductance value at a first location in the body lumen; moving the catheter to a second location in the body lumen; measuring a second conductance value at a second location in the body lumen; and determining a profile of the body lumen based on the first conductance value of the first location and the second conductance value of the second location. The profile of the body lumen resulting from such embodiments may include relative conductances and/or relative cross-sectional areas.

For other embodiments, the actual values for the lumen conductance or cross-sectional area are determined by further injecting a known volume of a first solution having a first conductivity into the body lumen; injecting a second solution having a second conductivity into the body lumen, wherein the second solution has a second volume and wherein the second conductivity does not equal the first conductivity; measuring a second conductance value at the first location in the body lumen; calculating the conductance at the first location in the body lumen; measuring a first conductance value at a second location in the body lumen; and calculating the conductance at the second location in the body lumen. The determination of the profile of the body lumen may be based on the conductance of the first location, the conductance of the second location, and the conductivities of the first and second solutions. In addition, in some embodiments, the tissue is ablated after localization using the same catheter for both aspects of the procedure.

BRIEF DESCRIPTION OF THE DRAWINGS

FIG. 3A shows an embodiment of a catheter for localization of a body lumen juncture;

FIG. 3B shows another embodiment of a catheter for localization of a body lumen juncture;

FIG. 3C shows an embodiment of a catheter for localization and ablation of a body lumen juncture;

FIG. 4A shows another embodiment of a catheter for localization;

FIG. 4B shows an embodiment of a balloon catheter having impedance measuring electrodes supported in front of the stenting balloon;

FIG. 4C shows another embodiment of a balloon catheter having impedance measuring electrodes within and in front of the balloon;

FIG. 4D shows an embodiment of a catheter having an ultrasound transducer within and in front of the balloon;

DETAILED DESCRIPTION

Figure 1:
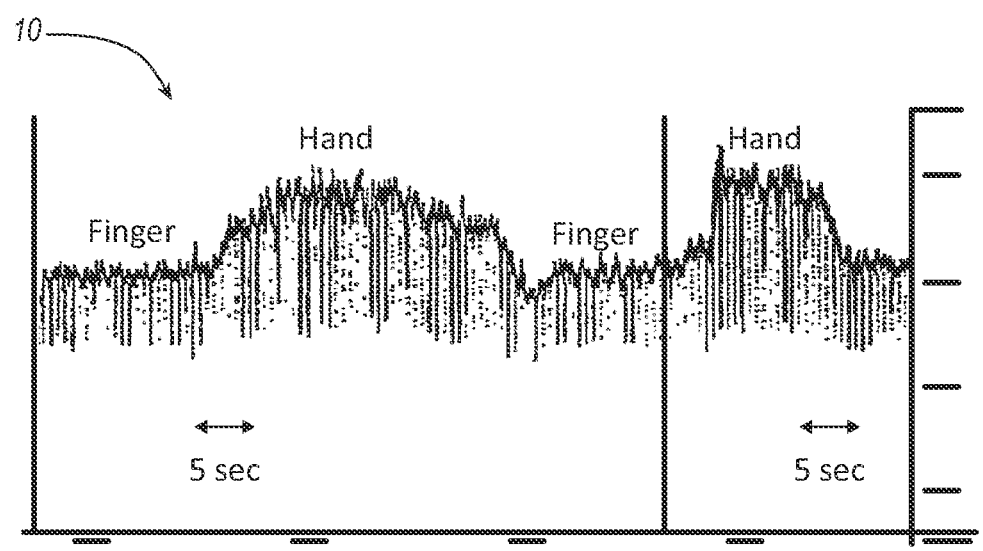
FIG. 1 shows the visual output of an embodiment of a catheter system for localization during an experiment of movement through an interior of a surgical glove.

It will be appreciated by those of skill in the art that the following detailed description of the disclosed embodiments is merely exemplary in nature and is not intended to limit the scope of the appended claims.

During various medical procedures involving intraluminal insertion of catheters or other devices, proper navigation of the device through body lumens, such as blood vessels or the heart, is critical to the success of the procedure. This is especially true with respect to catheterization of the aorta and coronary sinus. Indeed, unless the tissue targeted for treatment or diagnosis is properly located, the procedure can be ineffective or, even worse, damaging. For example, with respect to treatment of an aortic aneurysm, a stent must be delivered to a disease-free landing zone adjacent to the aneurysm. In the event the stent is inaccurately placed—due to disorientation within the lumen or otherwise—a sufficient seal will not be achieved and the treatment will be ineffective.

Similarly, in the treatment of ventricular fibrillation using CRT therapy, an electrical lead must be placed precisely within the coronary sinus through the ostium of the coronary sinus (the junction of the coronary sinus and the right atrium). Achieving the proper placement is an exceptionally difficult procedure, in part because there are various anatomical structures located within the right atrium that can be easily confused with the coronary sinus (e.g., the fossa ovalis, the custaclan ridge, etc.). These particular features of the heart do not show up well on a fluoroscope, therefore making the procedure quite difficult and time consuming for the clinician. Nevertheless, the clinician must be able to accurately insert the catheter into the coronary sinus without perforating the vessel or causing any trauma to the adjacent structures, all while the heart is beating. Having a clear map of the coronary sinus in the form of a lumen profile minimizes the risks involved with this procedure and drastically reduces the risk of damaging the surrounding structures. Accordingly, a number of the embodiments disclosed herein permit a clinician to readily locate a catheter, or other medical device, within a body lumen in relation to body lumen junctions or other anatomical structures within the lumen.

In addition to being able to properly navigate body lumens, it is also beneficial to obtain accurate measurements of the luminal cross-sectional area in a targeted location as this enables accurate and scientific stent sizing and placement. Obtaining such accurate measurements can improve clinical outcomes by avoiding under or over deployment and under or over sizing of a stent which can cause acute closure or in-stent restenosis. At least one embodiment disclosed herein allows a clinician to accurately measure the luminal cross-sectional area of an organ or body lumen. This leads to proper localization of a targeted tissue, accurate stent sizing and placement, and increased favorable outcomes for certain medical procedures.

In at least one embodiment, electrical conductance is measured within the body lumen and a profile of relative conductance values is displayed, while other embodiments use conductance data to calculate luminal cross-sectional areas and display a profile of relative cross-sectional areas along a portion of the lumen. These profiles enable the clinician to readily locate the targeted tissue for further treatment, such as for placement of a lead or stent.

Many of the disclosed embodiments do not calculate an absolute value for a lumen's cross-sectional area, but instead measure electrical conductance through a portion of the lumen to form a profile of the lumen. Often, the profile comprises relative conductances taken along the lumen. However, because conductance is proportional to cross-sectional area, as explained herein, the profile can comprise relative cross-sectional areas that have been determined from the conductances taken along the lumen.

By monitoring this profile during catheterization, the clinician can visualize the anatomical structure of the lumen. For example, using a push through or a pull back of a disclosed embodiment of a catheter through a lumen, a clinician is able to localize a junction or other architectural marker in the body lumen. Such a push through or pull back technique will reflect, in relative terms, the lumen's changes in conductance, and therefore its changes in cross-sectional area, as the catheter moves, thereby depicting changes in lumen structure across a distance. Based on such changes in lumen structure, a clinician can determine the locations of various anatomical markers of the lumen, as well as the location of the catheter in relation to those markers.

In one example, localization of the junction between an aortic aneurysm and the healthy aortic wall is achieved by assessing the change in conductance (and therefore in cross-sectional area) of the lumen as the catheter is pulled through the aorta and passes the affected tissue. Once a specific lumen junction or other anatomical structure is localized, the clinician can better treat a targeted tissue at or near that identifying structure. Such treatment may include, for example and without limitation, angioplasty or stent delivery. Further, because clinicians can accurately visualize the anatomic structure of the lumen, a catheter may be inserted into even the smallest blood vessel with a high degree of accuracy (e.g., the coronary sinus).

Experiments have demonstrated the ability of the disclosed embodiments to provide accurate and reliable feedback as to the location of a catheter within a body lumen. For instance, a surgical glove was filled with saline to simulate a left atrium (the palm) and pulmonary veins (the fingers). A catheter configured for localization as described herein was pulled back from inside a finger to the palm, thereby simulating the transition from a pulmonary vein to the atrium. FIG. 1 shows the conductance profile 10 as the catheter was pulled back from a finger into the palm of the glove, then was pushed into a finger. As can be seen, the profile shows that the conductance of the palm was significantly larger than the conductance of the finger, and the transition or demarcation from the finger to the palm is apparent. Because conductance and cross-sectional area ("CSA") are proportional (as discussed below), conductance profile 10 is proportional to the CSA profile (not shown) and distinguishes between the smaller cross-sectional area of the fingers and the larger cross-sectional area of the palm.

A similar pullback experiment was carried out in a heart. Starting from the pulmonary vein, a catheter configured for localization as described herein was pulled back from the pulmonary vein into the left atrium and ventricle. FIG. 2 shows a conductance tracing 12 that reflects the conductance for each region of the body lumen as the catheter is pulled back over a distance of about 5 cm from a starting point in the pulmonary vein. The pulmonary vein can be clearly identified by reference to its relative conductance compared to those of the left atrium, the mitral valve, and the left ventricle. Indeed, the atrial CSA is significantly larger than that of the pulmonary vein, and the atrial CSA increases with distance away from the pulmonary vein-atrial junction. A reduction in CSA is then observed as the catheter approaches and crosses the mitral valve. Once the catheter progresses through the mitral valve into the ventricle, the CSA increases gradually.

Figure 2A:
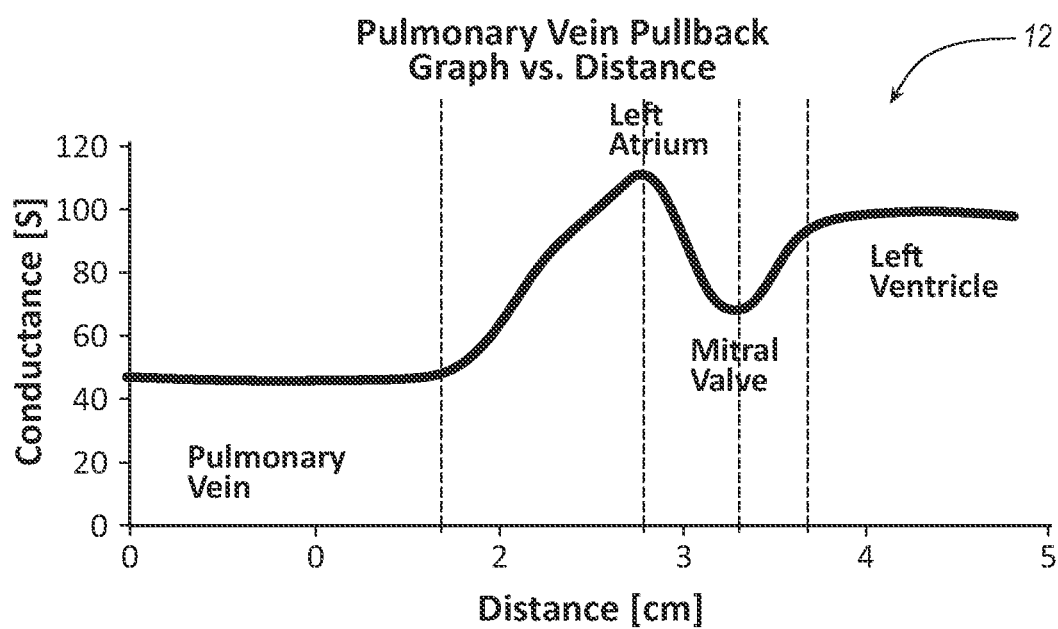
FIG. 2A shows the visual output of an embodiment of a catheter system for localization during an experiment of movement through an interior of a heart.

Using conductance data like that shown in FIG. 2, a clinician can precisely obtain his or her orientation within the aorta, and thereby localize an aortic aneurysm. For example, the various points of bifurcation of the aorta can be identified using the type of conductance data shown in FIG. 2A. Specifically, in FIG. 2A, where the conductance data begins to increase, the data indicates that the luminal CSA has increased, especially when such an increase is drastic.

A conductance or impedance catheter measures conductance within a body lumen using a number of electrodes. Referring now to FIG. 3A, there is shown a conductance catheter 400 configured to localize a body lumen junction using conductance measurements. Catheter 400 has a proximal end 405 and a distal end 410, which is suitable for introduction into a body lumen. In one embodiment, catheter 400 comprises a thin conductance wire that is capable of accessing the coronary sinus. In addition, catheter 400 includes a pair of excitation electrodes 415 and a pair of detection electrodes 420. Each of excitation electrodes 415 and detection electrodes 420 has a proximal end that is capable of attachment to a processing system (not shown) and a distal end that is located on catheter 400 between proximal end 405 and distal end 410. The distal ends of detection electrodes 420 are located on catheter 400 between the distal ends of excitation electrodes 415. Excitation electrodes 415 are configured to emit a measured electrical charge into the body lumen, while detection electrodes 420 detect the amount of the charge that travels through a fluid within the body lumen. As explained in more detail below, a processing system calculates the change in electrical charge to determine the conductance through the lumen at any given location in the lumen.

As shown in FIG. 3A, electrodes 415 and 420 are located at distal end 410 of catheter 400. However, the positioning of the electrodes is not limited to this distal end portion, but may be anywhere on the catheter that can assist in providing conductance information to the clinician. Furthermore, multiple sets of electrodes (see FIG. 4F) may also be used to provide additional information used for mapping the interior anatomical structure of an internal organ, vessel, or other body lumen.

A number of embodiments disclosed herein, such as the embodiment shown in FIG. 3A, have at least two detection electrodes and two excitation electrodes. However, in the embodiment shown in FIG. 3B, only two electrodes are used. Catheter 425 has a proximal end 430 and a distal end 435, as well as a first electrode 440 and a second electrode 445. Each of electrodes 440 and 445 has a proximal end (not shown) and a distal end located on catheter 425 between proximal end 430 and distal end 435. Because catheter 425 has only two electrodes, each electrode must serve both the excitation function and the detection function. To enable a single electrode to send and measure the electrical charge, a delay must be added to the circuit. Additionally, a bipolar catheter must be stationary at the time of measurement, requiring the clinician to obtain a profile by moving the catheter to a desired location, stopping and taking a measurement, and then moving the catheter again. By contrast, tetrapolar catheters may take a continuous conductance measurement as the catheter is pulled or pushed through the body lumen, thereby giving a more detailed profile as compared to bipolar catheters.

Although at least some embodiments can properly measure lumen conductance in the presence of a bodily fluid (such as blood) within the lumen, certain other embodiments may use fluids injected into the body lumen to properly calculate lumen conductance and/or cross-sectional area, as explained herein. Therefore, some embodiments include a channel through which fluid is injected into the body lumen. In the embodiment shown in FIG. 3C, infusion passageway 490 is configured to permit such injection so that fluid flowing from passageway 490 will flow at least to the location of the distal ends of excitation electrodes 470 and detection electrodes 480. Thus, the fluid passing through passageway 490 into the lumen will come in contact with the distal ends of excitation electrodes 470 and detection electrodes 480.

Referring now to FIGS. 4A to 4F, several embodiments of catheters are illustrated. With reference to the embodiment shown in FIG. 4A, there is shown an impedance catheter 22 with four electrodes 25, 26, 27, and 28 placed close to distal end 19 of the catheter. Electrodes 25 and 27 are excitation electrodes, while electrodes 26 and 28 are detection electrodes, thereby permitting measurement of conductance (and therefore calculation of cross-sectional area) during advancement of the catheter, as described in further detail below.

In addition, catheter 22 possesses an optional infusion passageway 35 located proximal to excitation electrode 25, as well as optional ports 36 for suction of contents of the body lumen or for infusion of fluid. The fluid to inject through passageway 35 or ports 36 can be any biologically compatible fluid, but, for some circumstances disclosed herein, the conductivity of the fluid is selected to be different from that of blood.

In various embodiments, including for example the embodiment shown in FIG. 4A, the catheter contains a channel 31 for insertion of a guide wire to stiffen the flexible catheter during insertion or data recording. Additionally, channel 31 may be used to inject fluid solutions of various concentrations (and various conductivities) into the body lumen of interest. An additional channel 32 may be connected to the catheter such that the electrical wires connected to the one or more electrodes on the catheter are directed through channel 32 and to a data processor, such as data processor system 100 (see FIG. 6), through an adaptor interface 33, such as an impedance module plug or the like, as described in more detail below.

In addition to localization, some embodiments disclosed herein provide other functionality. FIGS. 4B-4F show a number of embodiments of conductance catheters having various functions. For example, several such embodiments include an angioplasty balloon, in addition to impedance electrodes (see, e.g., FIG. 4B). Such catheters may include electrodes for accurate detection of organ luminal cross-sectional area and ports for pressure gradient measurements. Hence, when using such catheters, it is not necessary to change catheters during the procedure, as with the current use of intravascular ultrasound. In at least one embodiment, the catheter can provide direct measurement of the non-stenosed area of the lumen, thereby allowing the selection of an appropriately sized stent for implantation.

With reference to the embodiment shown in FIG. 4B, four wires are threaded through one of the two lumens of catheter 20 (a 4 Fr. catheter). Catheter 20 has a proximal end and a distal end 19, as well as excitation electrodes 25, 27 and detection electrodes 26, 28 placed at or near distal end 19. Proximal to these electrodes is an angioplasty or stenting balloon 30 capable of being used to treat stenosis. The distance between the balloon and the electrodes is usually small, in the 0.5 mm to 2 cm range, but can be closer or farther away, depending on the particular application or treatment involved. The portion of catheter 20 within balloon 30 includes an infusion passageway 35 and a pressure port 36.

Detection electrodes 26 and 28 are spaced 1 mm apart, while excitation electrodes 25 and 27 are spaced 4 mm to 5 mm from either side of the detection electrodes. The excitation and detection electrodes typically surround the catheter as ring electrodes, but they may also be point electrodes or have other suitable configurations. These electrodes may be made of any conductive material, such as platinum iridium or a material with a carbon-coated surface to avoid fibrin deposits. In at least one embodiment, the detection electrodes are spaced with 0.5 mm to 1 mm between them and with a distance of between 4 mm and 7 mm to the excitation electrodes on small catheters. On large catheters, for use in larger vessels and other larger body lumens, the electrode distances may be larger. The dimensions of the catheter selected for a treatment depend on the size of the vessel or other body lumen and are preferably determined in part on the results of finite element analysis.

In one approach, dimensions of a catheter to be used for any given application depend on the optimization of the potential field using finite element analysis described below. For small organs or in pediatric patients, the diameter of the catheter may be as small as 0.3 mm. In large organs, the diameter may be significantly larger depending on the results of the optimization based on finite element analysis. The balloon will typically be sized according to the preferred dimension of the organ after the distension. The balloon may be made of materials suitable for the function, such as, for example, polyethylene, latex, polyestherurethane, or combinations thereof. In at least one embodiment, the balloon comprises a thickness of a few microns. The catheter may comprise PVC or polyethylene material, although other materials may be used equally well. The tip of the catheter can be straight, curved, or angled to facilitate insertion into the coronary arteries or other body lumens, such as, for example, the biliary tract.

Referring again to FIG. 4B, catheter 20 may also include several miniature pressure transducers (not shown) carried by the catheter or pressure ports for determining the pressure gradient proximal to the site where the conductance is measured. The pressure is preferably measured inside the balloon and proximal to, distal to, and at the location of the conductance measurement, and locations proximal and distal thereto, thereby enabling the measurement of pressure recordings at the site of stenosis and also the measurement of pressure-difference along or near the stenosis. In one embodiment, shown in FIG. 4B, catheter 20 includes pressure port 90 and pressure port 91 proximal to or at the site of the conductance measurement for evaluation of pressure gradients. As described below with reference to FIGS. 5A, 5B, and 6, in at least one embodiment, the pressure ports are connected by respective conduits in catheter 20 to pressure sensors in the data processor system 100 (see FIG. 6). Such pressure sensors are well known in the art and include, for example, fiber-optic systems, miniature strain gauges, and perfused low-compliance manometry.

In at least one embodiment, a fluid-filled silastic pressure-monitoring catheter is connected to a pressure transducer. Luminal pressure can be monitored by a low compliance external pressure transducer coupled to the infusion channel of the catheter. Pressure transducer calibration was carried out by applying 0 and 100 mmHg of pressure by means of a hydrostatic column.

In another embodiment, shown in FIG. 4C, a catheter 39 includes another set of excitation electrodes 40, 41 and detection electrodes 42, 43 located inside the angioplastic or stenting balloon 30 for accurate determination of the balloon cross-sectional area during angioplasty or stent deployment. These electrodes are in addition to electrodes 25, 26, 27, and 28.

In various embodiments, the conductance may be measured using a two-electrode system (see FIG. 4D). In other embodiments, such as illustrated in FIG. 4F, the conductances at several locations can be measured at the same time using an array of five or more electrodes. Here, excitation electrodes 51, 52 are used to generate the current while detection electrodes 53, 54, 55, 56, and 57 are used to detect the current at their respective sites.

In another embodiment, shown in FIG. 4D, catheter 21 has one or more imaging or recording devices, such as, for example, ultrasound transducers 50 for cross-sectional area and wall thickness measurements. As shown, transducers 50 are located near distal end 19 of catheter 21.

Figure 4E:
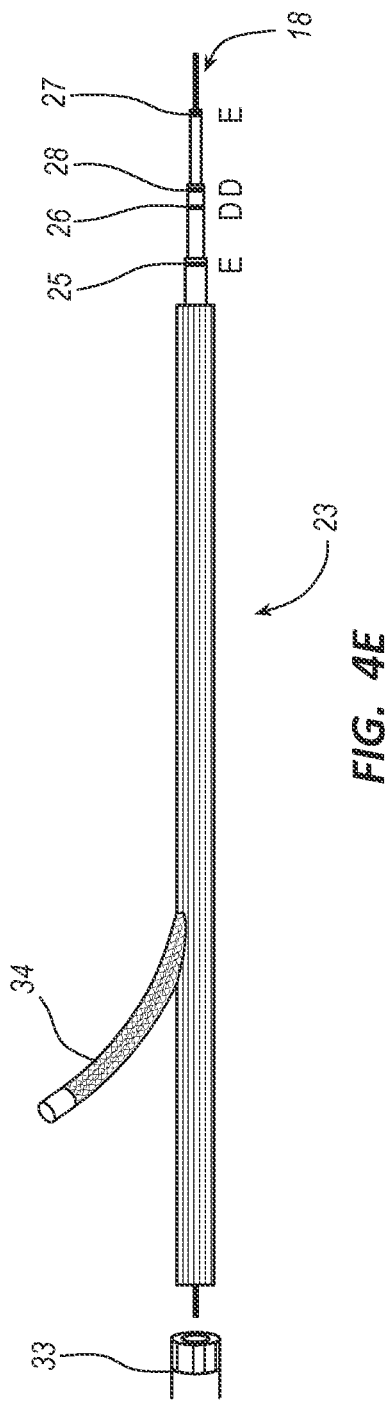
FIG. 4E shows an embodiment of a guide catheter with wire and impedance electrodes.
Figure 4F:
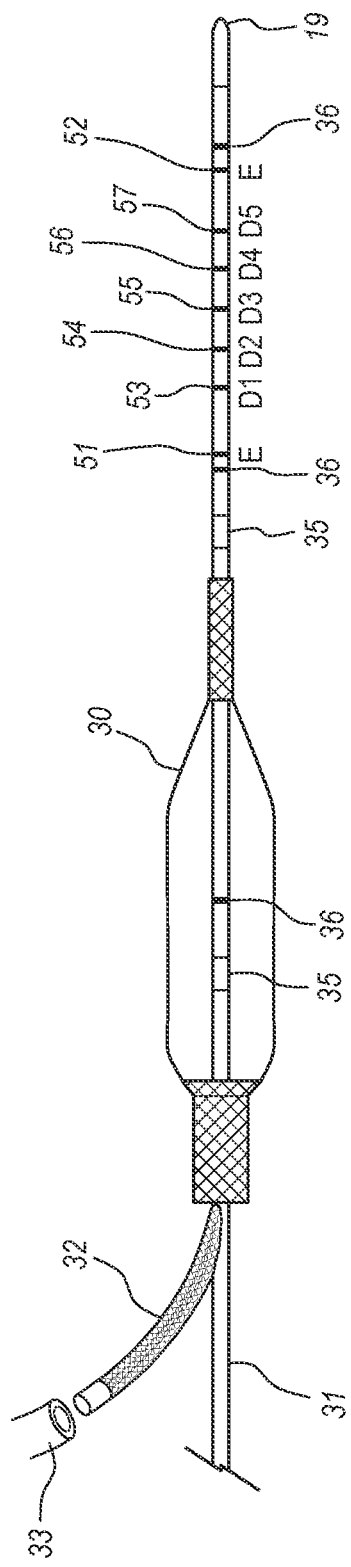
FIG. 4F shows an embodiment of a catheter with multiple detection electrodes.

With reference to the embodiment shown in FIG. 4E, electrodes 25, 26, 27, and 28 are built onto a wire 18, such as, for example, a pressure wire, and inserted through a guide catheter 23, where the infusion of a bolus can be made through the lumen of the guide catheter. Adaptor interface 33 may be used to house and guide the electrical wires (including proximal portions of the excitation and detection electrodes) to a data processor system 100, while a side channel 34 is used to inject various fluids into catheter 23. In yet another embodiment (not illustrated), the catheter includes a sensor for measurement of the flow of fluid in the body lumen.

Many of the embodiments described herein may be used as part of a system, which includes suitable connections between the system's various parts. As described below with reference to FIGS. 5A, 5B, and 6, the excitation and detection electrodes are electrically connected to electrically conductive leads in the catheter for connecting the electrodes to the data processor system 100.

Figure 5A:
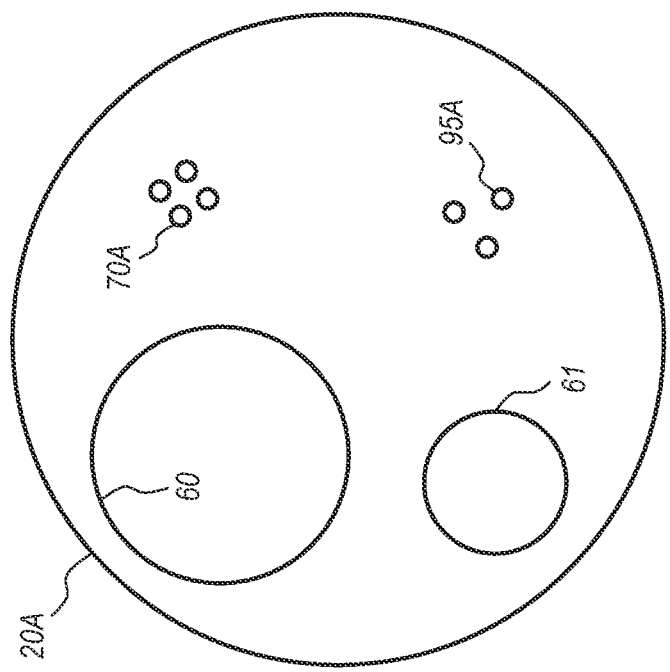
FIG. 5A shows an embodiment of a catheter in cross-section proximal to the location of the sensors showing the leads embedded in the material of the probe.
Figure 5B:
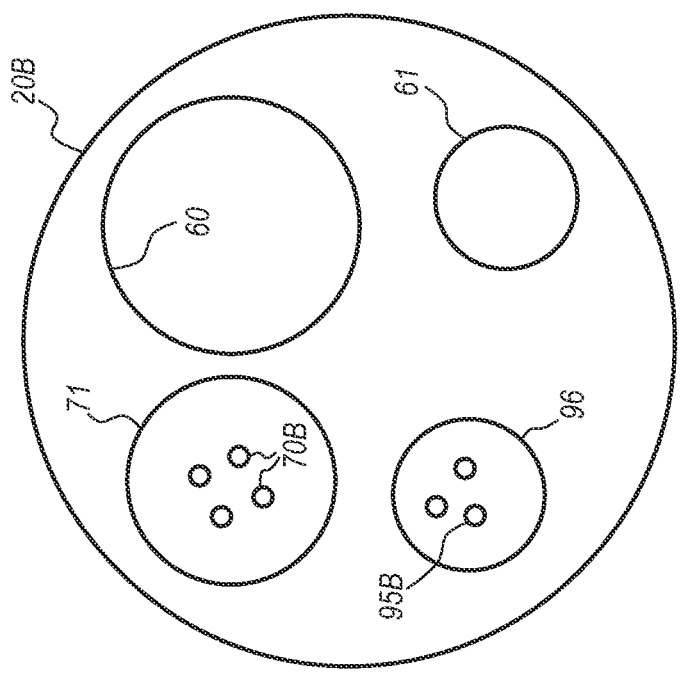
FIG. 5B shows another embodiment of a catheter in cross-section proximal to the location of the sensors showing the leads run in separate lumens.

FIGS. 5A and 5B illustrate cross-sectional views of two embodiments 20A and 20B of a catheter such as catheter 20 shown in FIG. 4B. Each embodiment has a lumen 60 for inflating and deflating the balloon and a lumen 61 for suction and infusion. The sizes of these lumens can vary. The electrode leads 70A are embedded in the material of the catheter in the embodiment shown in FIG. 5A, whereas the electrode leads 70B are tunneled through a lumen 71 formed within the body of catheter 20B shown in FIG. 5B.

Pressure conduits for perfusion manometry connect pressure ports 90, 91 to transducers included in the data processor system 100. As shown in FIG. 5A, pressure conduits 95A may be formed in catheter 20A. In another embodiment, shown in FIG. 5B, pressure conduits 95B constitute individual conduits within a tunnel 96 formed in catheter 20B. In the embodiments described above where miniature pressure transducers are carried by the catheter, electrical conductors may be substituted for these pressure conduits.

Figure 6:
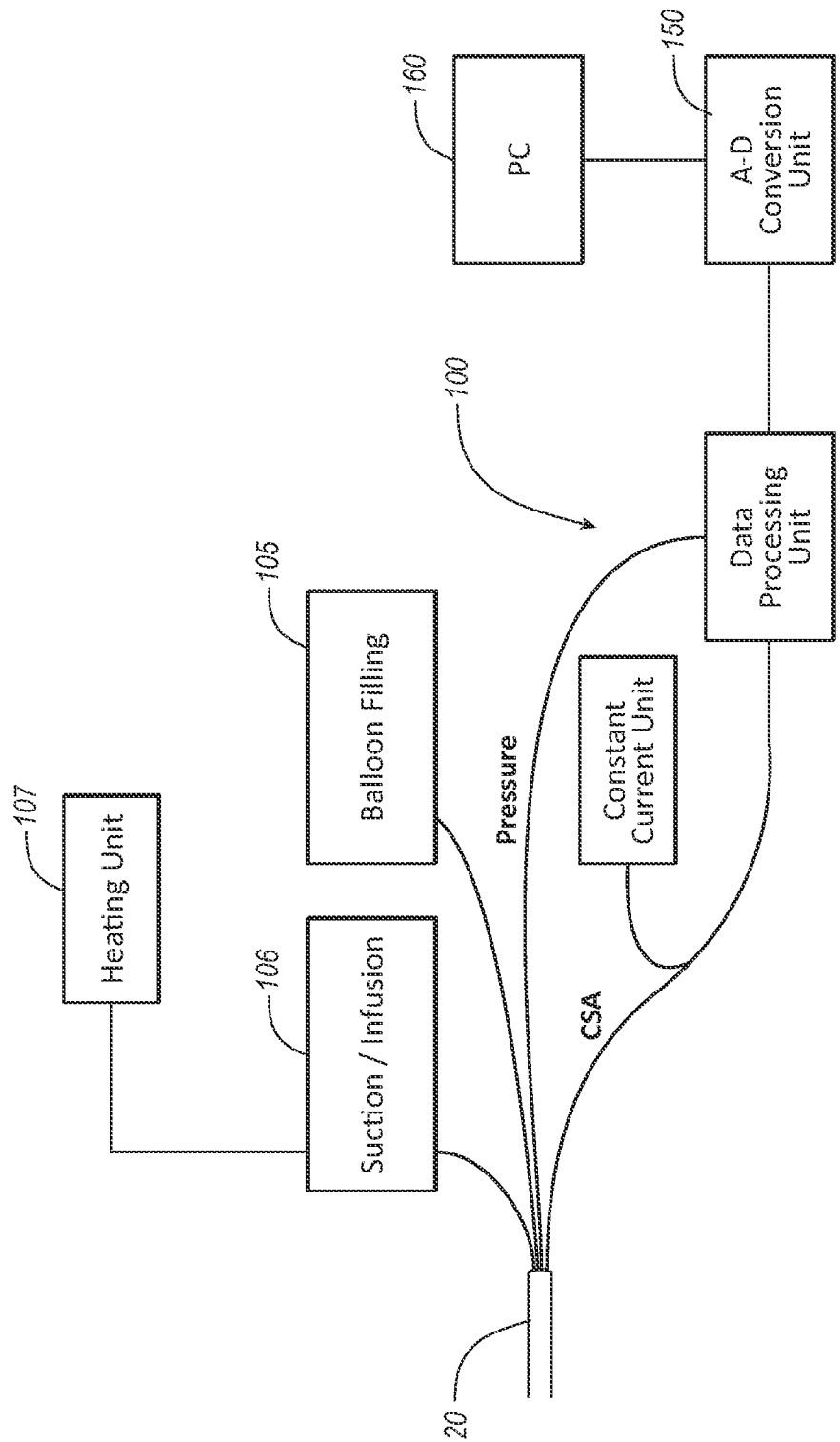
FIG. 6 is a schematic of an embodiment of a system showing a catheter carrying impedance measuring electrodes connected to a data processor equipment and excitation unit for the measurement of conductance and/or cross-sectional area.

With reference to FIG. 6, in at least some embodiments, catheter 20 connects to a data processor system 100, to a manual or automatic system 105 for distension of the balloon, and to a system 106 for infusion of fluid or suction of blood or other bodily fluid. The fluid for infusion may be heated with heating unit 107 to between 37° C. and 39° C. or to body temperature. The impedance planimetry system typically includes a constant current unit, amplifiers, and signal conditioners, but variations are possible. The pressure system typically includes amplifiers and signal conditioners. The system can optionally contain signal conditioning equipment for recording of fluid flow in the body lumen.

In at least one embodiment, the system is pre-calibrated and a catheter is available in a package. The package also may contain sterile syringes with fluids to be injected. The syringes are attached to the machine, and after heating of the fluid by the machine and placement of the catheter in the body lumen of interest, the user presses a button that initiates the injection with subsequent computation of the desired parameters. The CSA, parallel conductance, and/or other relevant measures, such as distensibility, tension, etc., will typically appear on the display panel in the PC module 160. The user can then treat the aortic aneurysm by placement of a stent.

If more than one CSA is measured at the same time, the system can contain a multiplexer unit or a switch between CSA channels. In at least one embodiment, each CSA measurement or pressure measurement will be through separate amplifier units.

In at least one embodiment, the impedance and pressure data are analog signals which are converted by analog-to-digital converters 150 and transmitted to a computer 160 for on-line display, on-line analysis, and storage. In other embodiments, all data handling is done on an entirely analog basis.

The processor system includes software programs for analyzing the conductance data. Additional software calculates cross-sectional areas based on a number of categories of data, as disclosed herein. However, as discussed in more detail below, to calculate for absolute cross-sectional values, certain errors must be reduced or eliminated. The software can be used to reduce the error in CSA values due to conductance of current in the lumen wall and surrounding tissue and to display the two-dimensional or three-dimensional geometry of the CSA distribution along the length of the vessel (and, optionally, along with the pressure gradient). In one embodiment of the software, a finite element approach or a finite difference approach is used to derive the CSA of organ stenosis, taking parameters such as conductivities of the fluid in the lumen and of the lumen wall and surrounding tissue into consideration.

In another embodiment, simpler circuits are used. As explained herein, absolute cross-sectional values may be calculated based on two or more injections of different NaCl solutions, which varies the conductivity of fluid in the lumen. In other embodiments, the software contains the code for reducing the error in luminal CSA measurement by analyzing signals during interventions, such as infusion of a fluid into the lumen or by changing the amplitude or frequency of the current from the current amplifier. The software chosen for a particular application may allow for computation of the CSA with only a small error instantly or within acceptable time during the medical procedure.

Referring now to FIG. 4A, catheter 22 measures conductance in the body lumen by detecting the change in voltage between detection electrodes 26, 28, as shown by the following equation:

$$\Delta V = \frac{I \cdot L}{C \cdot CSA} \quad [1a]$$

Thus, the change in voltage, $\Delta V$, is equal to the magnitude of the current, I, multiplied by the distance between the detection electrodes, L, divided by the conductivity of the fluid in the lumen, C, and divided by the cross-sectional area, CSA. Because the current (I), the distance (L), and the conductivity (C) normally can be regarded as calibration constants during a localization procedure, an inversely proportional relationship exists between the voltage difference and the CSA, as shown by the following equation:

$$\Delta V = \frac{I}{CSA} \quad [1b]$$

In other words, as the cross-sectional area of the lumen decreases, the change in voltage measured by catheter 22 increases. As discussed earlier, conductance and cross-sectional area are proportional. Thus, this equation permits the relative conductances or cross-sectional areas of various intralumen anatomical structures to be determined from measurement of the change in voltage across the lumen using at least one excitation electrode and one detection electrode.

Figure 2B:
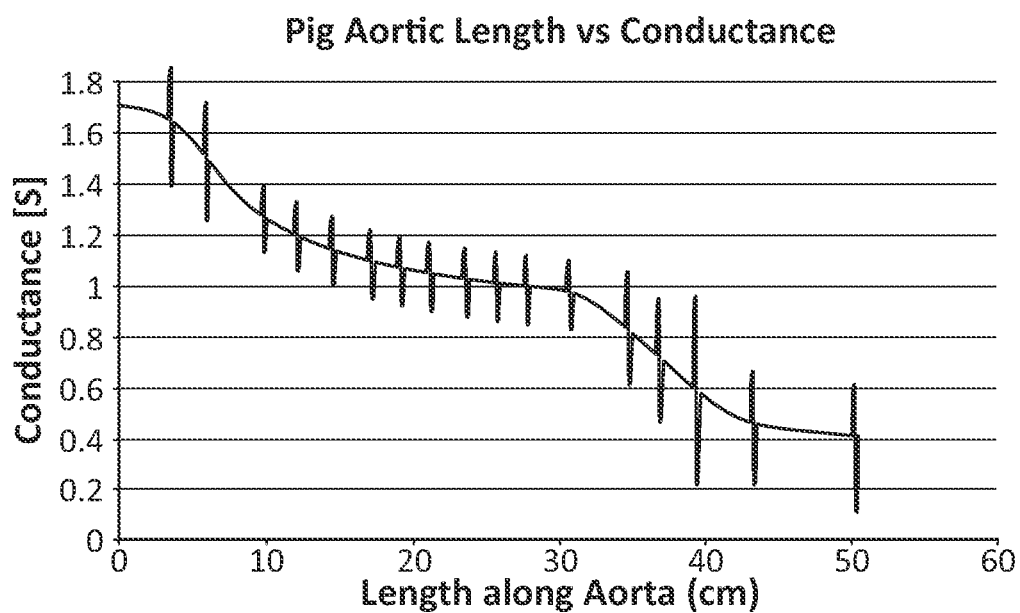
FIG. 2B shows a mean lumen profile of an aorta as generated by one embodiment of a catheter system for localization.
Figure 2C:
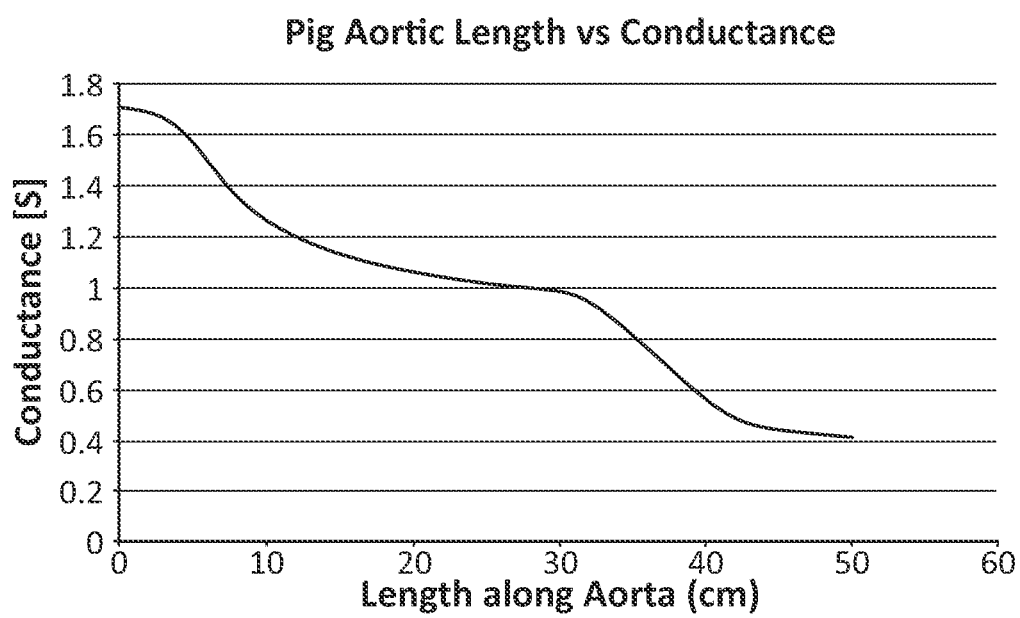
FIG. 2C shows a mean lumen profile of an aorta generated by one embodiment of a catheter system for localization and further comprising corrections for bifurcations.

This measurement, however, does not produce accurate, or absolute, values of conductance or CSA because the wall of the lumen and surrounding tissue effectuate a loss of current. Further, when the impedance electrode encounters a bifurcation, the measured conductance over estimates the segment area. This error is related to the dimension of the bifurcation and the angle of the branch, with an angle of 90° resulting in the largest error. As shown in FIG. 2B, the amplitude of the conductance is related to the size of the aortic branches; for example, the conductance spike (increase in conductance) resulting from the thoracic branches is smaller than the conductance spike formed when the catheter is pulled past the abdominal branches. Although relying on the relative conductances or CSAs is sufficient for the localization of intraluminal structures, other embodiments for other purposes may require the accurate determination of absolute values for CSAs.

At least some of the disclosed embodiments overcome the problems associated with determination of the size (cross-sectional area) of luminal organs, such as, for example, in the coronary arteries, carotid, femoral, renal and iliac arteries, aorta, gastrointestinal tract, urethra, and ureter. In addition, at least some embodiments also provide methods for registration of acute changes in wall conductance, such as, for example, due to edema or acute damage to the tissue, and for detection of muscle spasms/contractions.

The operation of catheter 20, shown in FIG. 4B, is as follows: for electrodes 25, 26, 27, 28, conductance of current flow through the organ lumen and organ wall and surrounding tissue is parallel; i.e., $$G(z, t) = \frac{CSA(z, t) \cdot C_b}{L} + G_p(z, t) \quad [2a]$$

where $G_p(z,t)$ is the effective conductance of the structure outside the bodily fluid (organ wall and surrounding tissue); $C_b$ is the specific conductivity of the bodily fluid, which for blood generally depends on the temperature, hematocrit and orientation and deformation of blood cells; and L is the distance between the detection electrodes. This equation shows that conductance, G(z,t), is proportional to the cross-sectional area, CSA(z,t). Thus, a larger conductance will reflect a larger cross-sectional area, and vice versa.

Equation [2a] can be rearranged to solve for cross sectional area CSA(z,t), with a correction factor, $\alpha$, if the electric field is non-homogeneous, as $$CSA(z, t) = \frac{L}{\alpha C_b}[G(z, t) - G_p(z, t)] \quad [2b]$$

where $\alpha$ would be equal to 1 if the field were completely homogeneous. The parallel conductance, $G_p$, is an offset error that results from current leakage. $G_p$ would equal 0 if all of the current were confined to the blood and hence would correspond to the cylindrical model given by Equation [1a]. In one approach, finite element analysis is used to properly design the spacing between detection and excitation electrodes relative to the dimensions of the body lumen to provide a nearly homogeneous field such that $\alpha$ can be considered equal to 1. Simulations show that a homogenous or substantially homogenous field is provided by (1) the placement of detection electrodes substantially equidistant from the excitation electrodes and (2) maintaining the distance between the detection and excitation electrodes substantially comparable to the body lumen diameter. In one approach, a homogeneous field is achieved by taking steps (1) and/or (2) described above so that $\alpha$ is equals 1 in the foregoing analysis.

$G_p$ is a constant at any given position, z, along the long axis of a body lumen, and at any given time, t, in the cardiac cycle. Hence, two injections of different concentrations (and therefore conductivities) of NaCl solution give rise to two equations:

$$C_1 \cdot CSA(z,t) + L \cdot G_p(z,t) = L \cdot G_1(z,t) \quad [3]$$

$$C_2 \cdot CSA(z,t) + L \cdot G_p(z,t) = L \cdot G_2(z,t) \quad [4]$$

which can be solved simultaneously for CSA and $G_p$ as $$CSA(z, t) = L \frac{[G_2(z, t) - G_1(z, t)]}{[C_2 - C_1]} \quad [4]$$

$$G_p(z, t) = \frac{[C_2 \cdot G_1(z, t) - C_1 \cdot G_2(z, t)]}{[C_2 - C_1]} \quad [5]$$

where subscript "1" and subscript "2" designate any two injections of different NaCl concentrations (and conductivities). For each injection k, $C_k$ gives rise to $G_k$ which is measured as the ratio of the root mean square of the current divided by the root mean square of the voltage. The $C_k$ is typically determined through in vitro calibration for the various NaCl concentrations. The concentration of NaCl used is typically on the order of 0.45 to 1.8%. The volume of NaCl solution is typically about 5 ml, but the amount of solution should be sufficient to momentarily displace the entire local vascular blood volume or other body lumen fluid. The values of CSA(t) and $G_p$(t) can be determined at end-diastole or end-systole (i.e., the minimum and maximum values) or the mean thereof. The value of CSA would vary through the cardiac cycle, but $G_p$(t) does not vary significantly.

Once the CSA and $G_p$ of the body lumen are determined according to the above embodiment, rearrangement of Equation [2a] allows the calculation of the specific electrical conductivity of bodily fluid in the presence of fluid flow as $$C_b = \frac{L}{CSA(z, t)}[G(z, t) - G_p(z, t)] \quad [7]$$

In this way, Equation [2b] can be used to calculate the CSA continuously (temporal variation, as for example through the cardiac cycle) in the presence of bodily fluid.

In one approach, a pull or push through is used to reconstruct the body lumen CSA along its length. During a long injection (e.g., 10 s to 15 s), the catheter can be pulled back or pushed forward at constant velocity, U. Equation [2a] can be expressed as $$CSA(U \cdot t, t) = \frac{L}{C_b}[G(U \cdot t, t) - G_p(U \cdot (t, t)] \quad [8]$$

where the axial position, z, is the product of catheter velocity, U, and time, t; i.e., z=U·t.

For the two injections, denoted by subscript "1" and subscript "2", respectively, different time points $T_1$, $T_2$, etc., may be considered such that Equation [8] can be written as $$CSA_1(U \cdot T_1, t) = \frac{L}{C_1}[G_1(U \cdot T_1, t) - G_{p1}(U \cdot T_1, t)] \quad [9a]$$

$$CSA_1(U \cdot T_1, t) = \frac{L}{C_2}[G_2(U \cdot T_1, t) - G_{p1}(U \cdot T_1, t)] \quad [9b]$$

and $$CSA_2(U \cdot T_2, t) = \frac{L}{C_1}[G_1(U \cdot T_2, t) - G_{p2}(U \cdot T_2, t)] \quad [10a]$$

$$CSA_2(U \cdot T_2, t) = \frac{L}{C_2}[G_2(U \cdot T_2, t) - G_{p2}(U \cdot T_2, t)] \quad [10b]$$

and so on. Each set of Equations [9a], [9b] and [10a], [10b], etc. can be solved for $CSA_1$, $G_{p1}$ and $CSA_2$, $G_{p2}$, respectively. Hence, one can measure the CSA at various time intervals and therefore at different positions along the body lumen to reconstruct the length of the lumen. In at least one embodiment, the data on the CSA and parallel conductance as a function of longitudinal position along the body lumen can be exported from an electronic spreadsheet, such as, for example, a Microsoft Excel file, to diagramming software, such as AutoCAD®, where the software uses the coordinates to render a three-dimensional depiction of the lumen on the monitor.

For example, in one approach, the pull back reconstruction was made during a long injection where the catheter was pulled back at constant rate by hand. The catheter was marked along its length such that the pull back was made at 2 mm/sec. Hence, during a 10-second injection, the catheter was pulled back about 2 cm. The data was continuously measured and analyzed at every two second interval; i.e., at every 4 mm. Thus, six different measurements of CSA and $G_p$ were taken which were used to reconstruct the CSA and $G_p$ along the length of the 2 cm segment.

In an additional embodiment, the wall thickness is determined from the parallel conductance for those body lumens that are surrounded by air or non-conducting tissue. In such cases, the parallel conductance is equal to $$G_p = \frac{CSA_w \cdot C_w}{L} \quad [11a]$$

where $CSA_w$ is the CSA of the lumen wall and $C_w$ is the electrical conductivity of the wall. This equation can be solved for $CSA_w$ as $$CSA_w = \frac{G_p \cdot L}{C_w} \quad [11b]$$

For a cylindrical body lumen, the wall thickness, h, can be expressed as $$h = \frac{CSA_w}{\pi D} \quad [12]$$

where D is the diameter of the lumen, which can be determined from the circular $CSA(D=[4CSA/\pi]^{1/2})$.

When the CSA, pressure, wall thickness, and flow data are determined according to the embodiments outlined above, it is possible to compute the compliance (e.g., $\Delta CSA/\Delta P$), tension (e.g., P*r, where P and r are the intraluminal pressure and radius of a cylindrical organ), stress (e.g., P*r/h where h is the wall thickness of the cylindrical organ), strain (e.g., $(C-C_d)/C_d$ where C is the inner circumference and $C_d$ is the circumference in diastole) and wall shear stress (e.g., $4\mu Q/r^3$ where $\mu$, Q and r are the fluid viscosity, flow rate and radius of the cylindrical organ, respectively, for a fully developed flow). These quantities can be used in assessing the mechanical characteristics of the system in health and disease.

In at least one approach for localization or measuring the conductance (and determining the cross-sectional area) of a body lumen, a catheter is introduced from an exteriorly accessible opening (for example, the mouth, nose, or anus for GI applications, or the mouth or nose for airway applications) into the targeted body lumen. For cardiovascular applications, the catheter can be inserted into the lumens in various ways, such as, for example, those used in conventional angioplasty. In at least one embodiment, an 18 gauge needle is inserted into the femoral artery followed by an introducer. A guide wire is then inserted into the introducer and advanced into the lumen of the femoral artery. A 4 or 5 Fr. conductance catheter is then inserted into the femoral artery via wire, and the wire is subsequently retracted. The catheter tip containing the conductance electrodes can then be advanced to the region of interest by use of x-ray (e.g., fluoroscopy). In another approach, this methodology is used on small to medium size vessels (e.g., femoral, coronary, carotid, iliac arteries).

In another embodiment, error due to the loss of current in the wall of the organ and surrounding tissue is corrected by injection of two solutions of NaCl or other solutions with known conductivities. In one approach, a minimum of two injections with different concentrations of NaCl (and, therefore, different conductivities) are required to solve for the two unknowns, CSA and $G_p$. However, in other embodiments disclosed herein, only relative values for conductance or cross-sectional area are necessary, so the injection of two solutions is not necessary. In another approach, three injections will yield three sets of values for CSA and $G_p$ (although not necessarily linearly independent), while four injections would yield six sets of values. In one approach, at least two solutions (e.g., 0.5% and 1.5% NaCl solutions) are injected in the targeted vessel or other lumen. Studies indicate that an infusion rate of approximately 1 ml/s for a five second interval is sufficient to displace the blood volume and results in a local pressure increase of less than 10 mmHg in the coronary artery. This pressure change depends on the injection rate which should be comparable to the lumen flow rate.

In at least one approach, involving the application of Equations [5] and [6], the vessel is under identical or very similar conditions during the two injections. Hence, some variables, such as the infusion rate, bolus temperature, etc., are similar for the two injections. Typically, a short time interval is to be allowed (1 to 2 minute period) between the two injections to permit the vessel to return to homeostatic state. This can be determined from the baseline conductance as shown in FIGS. 7A, 7B, 8A, or 8B. The parallel conductance is preferably the same or very similar during the two injections. Dextran, albumin, or another large molecular weight molecule may be added to the NaCl solutions to maintain the colloid osmotic pressure of the solution to reduce or prevent fluid or ion exchange through the vessel wall.

In yet another embodiment, the NaCl solution is heated to body temperature prior to injection since the conductivity of current is temperature dependent. Alternatively, the injected bolus is at room temperature, but a mathematical temperature correction is made since the conductivity is related to temperature in a linear fashion.

In one approach, a sheath is inserted through either the femoral artery or the carotid artery in the direction of flow. To access the lower anterior descending ("LAD") artery, the sheath is inserted through the ascending aorta. For the carotid artery, where the diameter is typically on the order of 5 mm to 5.5 mm, a catheter having a diameter of 1.9 mm can be used, as determined from finite element analysis, discussed further below. For the femoral and coronary arteries, where the diameter is typically in the range from 3.5 mm to 4 mm, so a catheter of about 0.8 mm diameter would be appropriate. The catheter can be inserted into the femoral, carotid, or LAD artery through a sheath appropriate for the particular treatment. Measurements for all three vessels can be made similarly.

At least one clinical application of the embodiments of the systems and methods disclosed herein relates to the delivery of pacing leads used in CRT, and, in particular, the delivery of a coronary sinus lead. When CRT is employed, it is necessary to advance a lead into the coronary sinus and coronary veins branching therefrom in order to position the electrode(s) adjacent to the left ventricle of the heart. During delivery, the distal end of the coronary lead is advanced through the superior vena cava, the right atrium, the valve of the coronary sinus, the coronary sinus, and may be further advanced into a coronary vein communicating with the coronary sinus, such as the great cardiac vein. Routing a lead along the desired path to implant the electrode in the desired implantation site can be difficult. This is particularly true with respect to steering leads through the coronary sinus and into a branching vein on the left myocardium (posterior lateral branch). The relatively small diameter of the coronary veins of the heart, the various anomalies typical in vascular anatomy, and the number of branch veins associated with the anatomy make locating the desired path challenging. Using the catheters and systems disclosed herein, it is possible to obtain precise measurements of the coronary sinus and related branching blood vessels, to facilitate the navigation of such difficult areas. In other words, the catheters and systems disclosed herein can obtain an accurate profile of the coronary venous system, including accurate identification of bifurcations along the length of the coronary sinus.

In at least one embodiment, a conductance catheter comprising a thin wire may be employed for delivering a lead into the coronary sinus or a bifurcation branching therefrom. In this embodiment, the conductance wire can be pulled through the coronary sinus and used to create a conductance profile thereof. In this manner, a clinician can accurately identify—with a high degree of specificity—the various bifurcations branching from the coronary sinus. The clinician can identify the bifurcation of interest and thereafter steer the conductance wire therein. Once the wire is positioned within the bifurcation, the lead can be inserted over the wire and placed within the desired bifurcation. This application can be conducted using the larger conductance catheters described herein as well; however, the relatively small diameter of a conductance catheter comprising a wire facilitates navigation through the narrow bifurcations branching from the coronary sinus.

Described herein are the protocol and results for one approach that are generally applicable to most arterial vessels. The conductance catheter was inserted through the sheath for a particular vessel of interest. A baseline reading of voltage was continuously recorded. Two containers containing 0.5% and 1.5% NaCl were placed in temperature bath and maintained at 37° C. A 5 ml to 10 ml injection of 1.5% NaCl was made over a 5 second interval. The detection voltage was continuously recorded over a 10 second interval during the 5 second injection. Several minutes later, a similar volume of 1.5% NaCl solution was injected at a similar rate. The data was again recorded. Matlab® was used to analyze the data including filtering with high pass and with low cut off frequency (1200 Hz). The data was displayed using Matlab®, and the mean of the voltage signal during the passage of each respective solution was recorded. The corresponding currents were also measured to yield the conductance (G=I/V). The conductivity of each solution was calibrated with six different tubes of known CSA at body temperature. A model using Equation [1a] was fitted to the data to calculate conductivity C. The analysis was carried out with SPSS statistical software using the non-linear regression fit. Given C and G for each of the two injections, an Excel spreadsheet file was formatted to calculate the CSA and $G_p$ as per equations [5] and [6], respectively. These measurements were repeated several times to determine the reproducibility of the technique. The reproducibility of the data was within 5%. Ultrasound was used to measure the diameter of the vessel simultaneous with our conductance measurements. The detection electrodes were visualized with ultrasound, and the diameter measurements was made at the center of the detection electrodes. The maximum differences between the conductance and ultrasound measurements were within 10%.

FIGS. 7A, 7B, 8A, and 8B illustrate voltage measurements in the blood stream in the left carotid artery. Here, the data acquisition had a sampling frequency of 75 KHz, with two channels—the current injected and the detected voltage, respectively. The current injected has a frequency of 5 KHz, so the voltage detected, modulated in amplitude by the impedance changing through the bolus injection, will have a spectrum in the vicinity of 5 KHz.

Figure 7A:
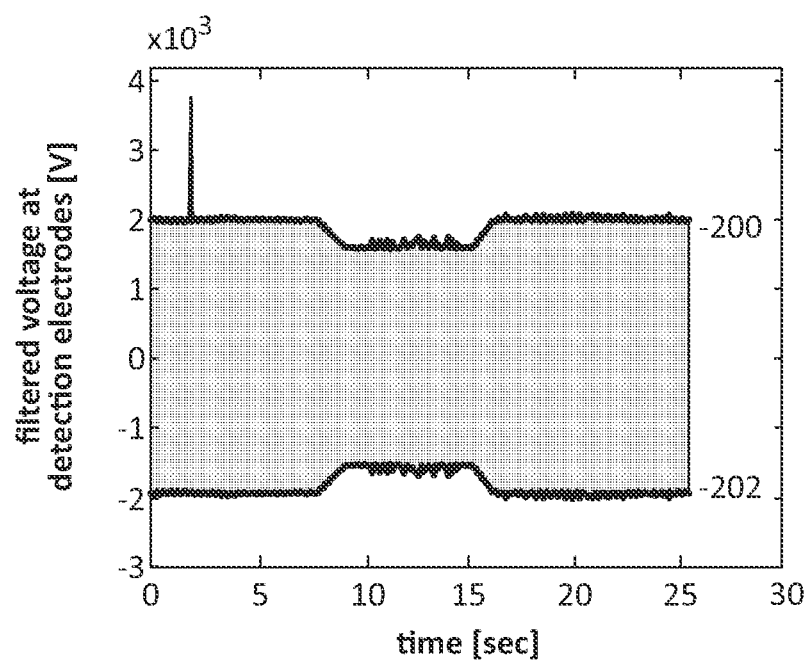
FIG. 7A shows the detected filtered voltage drop as measured in the blood stream before and after injection of 1.5% NaCl solution.
Figure 7B:
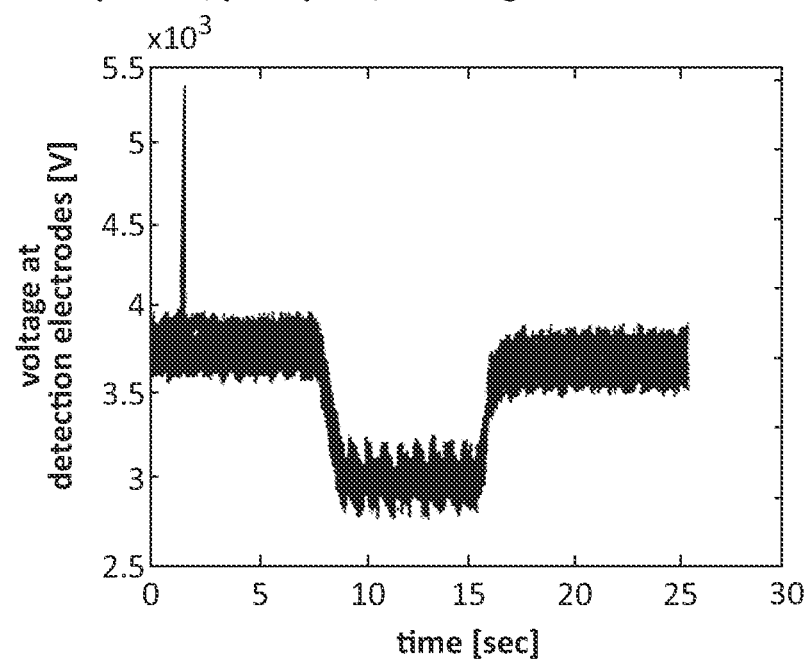
FIG. 7B shows the peak-to-peak envelope of the detected voltage shown in FIG. 7A.
Figure 8A:
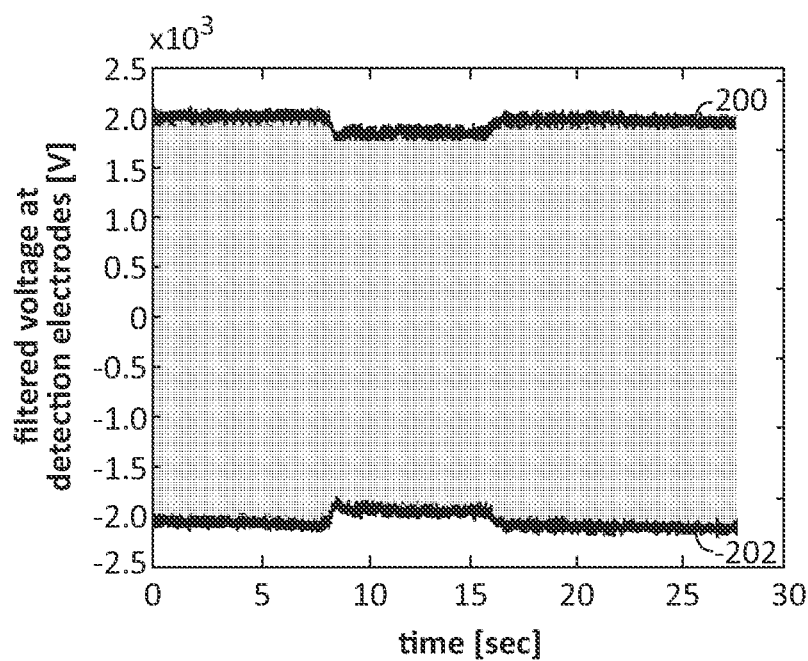
FIG. 8A shows the detected filtered voltage drop as measured in the blood stream before and after injection of 0.5% NaCl solution.
Figure 8B:
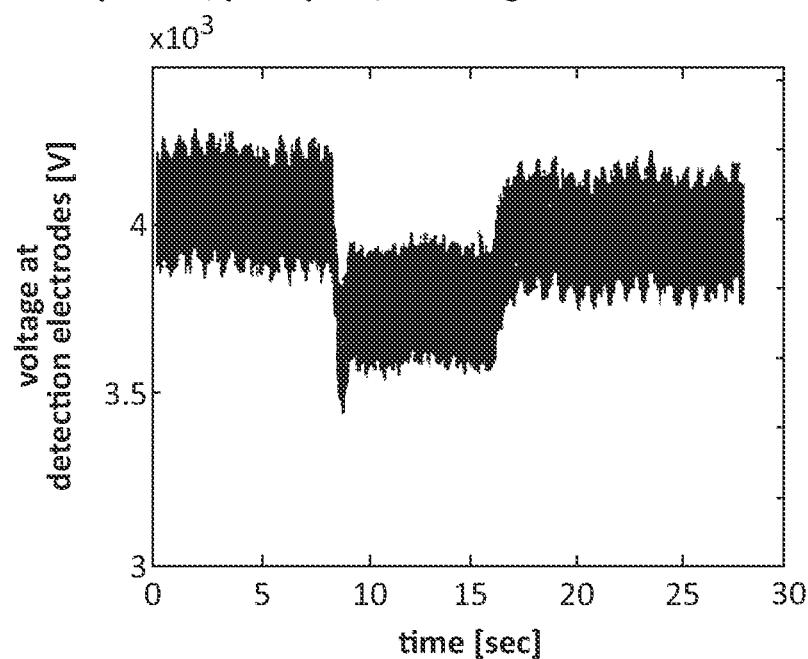
FIG. 8B shows the peak-to-peak envelope of the detected voltage shown in FIG. 8A.

With reference to FIG. 7A there is shown a signal processed with a high pass filter with low cut off frequency (1200 Hz). The top and bottom portions 200, 202 show the peak-to-peak envelope detected voltage which is displayed in FIG. 7B. The initial 7 seconds correspond to the baseline; i.e., electrodes in the blood stream. The next 7 seconds correspond to an injection of hyper-osmotic NaCl solution (1.5% NaCl). It can be seen that the voltage is decreased, implying increased conductance (since the injected current is constant). Once the NaCl solution is washed out, the baseline is recovered as shown in FIGS. 7A and 7B. FIGS. 8A and 8B show similar data corresponding to 0.5% NaCl solutions.

The voltage signals are ideal since the difference between the baseline and the injected solution is apparent and systematic. Furthermore, the pulsation of vessel diameter can be seen in the 0.5% and 1.5% NaCl injections (FIGS. 7A, 7B and 8A, 8B, respectively). This allows determination of the variation of CSA throughout the cardiac cycle as outline above.

The NaCl solution can be injected by hand or by using a mechanical injector to momentarily displace the entire volume of blood or bodily fluid in the lumen segment of interest. For example, in a blood vessel, the pressure generated by the injection will not only displace the blood in the antegrade direction (in the direction of blood flow) but also in the retrograde direction (by momentarily pushing the blood backwards). In other visceral organs which may be normally collapsed, the NaCl solution will not displace blood as in the vessels but will merely open the organs and create a flow of the fluid. In one approach, after injection of a first solution into the treatment or measurement site, sensors monitor and confirm baseline of conductance prior to injection of a second solution into the treatment site.

The injections described above are preferably repeated at least once to reduce errors associated with the administration of the injections, such as, for example, where the injection does not completely displace the blood or where there is significant mixing with blood. As previously noted, any bifurcation(s) (with branching angle near 90°) near the targeted lumen can cause an overestimation of the calculated CSA, thereby resulting in a conductance spike (see FIG. 2B). Hence, generally the catheter should be slightly retracted or advanced and the measurement repeated. An additional application with multiple detection electrodes or a pull back or push forward during injection will accomplish the same goal. Here, an array of detection electrodes can be used to minimize or eliminate errors that would result from bifurcations or branching in the measurement or treatment site.

In at least one embodiment, conductance spikes when present can be eliminated or smoothed out through a number or computational processing means, including, without limitation, threshold limits, gradient, interpolation, and smoothing algorithms. Threshold limits can be programmed to ignore readings for points where the cross-sectional area is greater than a preset number. Threshold limits are convenient to program; however, using solely threshold limits will not allow for differentiation between bifurcations caused by luminal branches and those caused by conditions such as aneurysms. Accordingly, consideration of the gradient (slope) where a conductance spike would correspond to a large, or possibly infinite, gradient. This criterion can be used in conjunction with a smoothing algorithm (e.g., linear interpolation or cubic spline) to distinguish a bifurcation from a pathological condition. Now referring to FIG. 2C, the data of FIG. 2B is shown after the conductance spikes have been eliminated using at least one computational processing means. Similar profiles can be generated for the coronary sinus and, as such, the effective and convenient navigation thereof can be achieved. The width of the conductance spike (not shown) can represent the approximate size (or diameter) of the bifurcation.

In an alternative approach, error due to the eccentric position of the electrode or other imaging device can be reduced by inflation of a balloon on the catheter. The inflation of the balloon during measurement will place the electrodes or other imaging device in the center of the vessel away from the wall. In the case of impedance electrodes, the inflation of the balloon can be synchronized with the injection of a bolus such that the balloon inflation would immediately precede the bolus injection. Our results, however, show that the error due to catheter eccentricity is small.

The CSA predicted by Equation [5] corresponds to the area of the vessel or other lumen external to the catheter (i.e., CSA of vessel minus CSA of catheter). If the conductivity of the NaCl solutions is determined by calibration from Equation [1a] with various tubes of known CSA, then the calibration accounts for the dimension of the catheter and the calculated CSA corresponds to that of the total vessel lumen. In at least one embodiment, the calibration of the CSA measurement system will be performed at 37° C. by applying 100 mmHg in a solid polyphenolenoxide block with holes of known CSA ranging from 7.065 mm$^2$ (3 mm in diameter) to 1017 mm$^2$ (36 mm in diameter). However, if the conductivity of the solutions is obtained from a conductivity meter independent of the catheter, then the CSA of the catheter is generally added to the CSA computed from Equation [5] to give the total CSA of the vessel.

The signals are generally non-stationary, nonlinear, and stochastic. To deal with non-stationary stochastic functions, one can use a number of methods, such as the Spectrogram, the Wavelet's analysis, the Wigner-Ville distribution, the Evolutionary Spectrum, Modal analysis, or the intrinsic model function ("IMF") method. The mean or peak-to-peak values can be systematically determined by the aforementioned signal analysis and used in Equation [5] to compute the CSA.

For the determination of conductance or cross-sectional area of a heart valve, it is generally not feasible to displace the entire volume of the heart. Hence, the conductivity of the blood is transiently changed by injection of a hypertonic NaCl solution into the pulmonary artery. If the measured total conductance is plotted versus blood conductivity on a graph, the extrapolated conductance at zero conductivity corresponds to the parallel conductance. In order to ensure that the two inner electrodes are positioned in the plane of the valve annulus (2 mm to 3 mm), in one embodiment, two pressure sensors 36 are placed immediately proximal and distal to (1 mm to 2 mm above and below, respectively) the detection electrodes or sets of detection electrodes (see, e.g., FIGS. 4A and 4F). The pressure readings will then indicate the position of the detection electrode relative to the desired site of measurement (aortic valve: aortic-ventricular pressure; mitral valve: left ventricular-atrial pressure; tricuspid valve: right atrial-ventricular pressure; pulmonary valve: right ventricular-pulmonary pressure). The parallel conductance at the site of annulus is generally expected to be small since the annulus consists primarily of collagen, which has low electrical conductivity. In another application, a pull back or push forward through the heart chamber will show different conductance due to the change in geometry and parallel conductance. This can be established for normal patients, which can then be used to diagnose valvular stenosis.

In one approach, for the esophagus or the urethra, the procedures can conveniently be done by swallowing fluids of known conductivities into the esophagus and infusion of fluids of known conductances into the urinary bladder followed by voiding the volume. In another approach, fluids can be swallowed or urine voided followed by measurement of the fluid conductivities from samples of the fluid. The latter method can be applied to the ureter where a catheter can be advanced up into the ureter and fluids can be injected from a proximal port on the probe (will also be applicable in the intestines) or urine production can be increased and samples taken distal in the ureter during passage of the bolus or from the urinary bladder.

In one approach, concomitant with measuring the conductance, cross-sectional area, and/or pressure gradient at the treatment or measurement site, a mechanical stimulus is introduced by way of inflating the balloon or by releasing a stent from the catheter, thereby facilitating flow through the stenosed part of the lumen.

In another approach, concomitant with measuring the conductance, cross-sectional area, and/or pressure gradient at the treatment site, one or more pharmaceutical substances for diagnosis or treatment of stenosis is injected into the treatment site. For example, in one approach, the injected substance can be a smooth muscle agonist or antagonist. In yet another approach, concomitant with measuring the conductance, cross-sectional area, and/or pressure gradient at the treatment site, an inflating fluid is released into the treatment site for release of any stenosis or materials causing stenosis in the lumen or treatment site.

Again, it will be noted that the methods, systems, and catheters described herein can be applied to any body lumen or treatment site. For example, the methods, systems, and catheters described herein can be applied to any one of the following hollow bodily systems: the cardiovascular system including the heart; the digestive system; the respiratory system; the reproductive system; and the urogenital tract.

Finite Element Analysis: In one preferred approach, finite element analysis ("FEA") is used to verify the validity of Equations [5] and [6]. There are two major considerations for the model definition: geometry and electrical properties. The general equation governing the electric scalar potential distribution, V, is given by Poisson's equation as:

$$\nabla \cdot (C \nabla V) = -I \quad [13]$$

where C, I, and $\nabla$ are the conductivity, the driving current density, and the del operator, respectively. Femlab or any standard finite element package can be used to compute the nodal voltages using Equation [13]. Once V has been determined, the electric field can be obtained from $E = -\nabla V$.

The FEA allows for the determination of the nature of the field and its alteration in response to different electrode distances, distances between driving electrodes, wall thicknesses, and wall conductivities. The percentage of total current in the lumen of the vessel (% I) can be used as an index of both leakage and field homogeneity. Hence, the various geometric and electrical material properties can be varied to obtain the optimum design, i.e. minimizing the non-homogeneity of the field. Furthermore, the experimental procedure was simulated by injection of the two solutions of NaCl to verify the accuracy of Equation [5]. Finally, the effect of the presence of electrodes and the catheter in the lumen of vessel was assessed. The error terms representing the changes in measured conductance due to the attraction of the field to the electrodes and the repulsion of the field from the resistive catheter body were quantified.

Poisson's equation was solved for the potential field, which takes into account the magnitude of the applied current, the location of the current driving and detection electrodes, and the conductivities and geometrical shapes in the model including the vessel wall and surrounding tissue. This analysis suggests that the following conditions are optimal for the cylindrical model: (1) the placement of detection (voltage sensing) electrodes equidistant from the excitation (current driving) electrodes; (2) the distance between the excitation electrodes should be much greater than the distance between the detection electrodes; and (3) the distance between the detection and excitation electrodes is comparable to the vessel diameter, or the diameter of the vessel is small relative to the distance between the driving electrodes. If these conditions are satisfied, the equipotential contours more closely resemble straight lines perpendicular to the axis of the catheter and the voltage drop measured at the wall will be nearly identical to that at the center. Since the curvature of the equipotential contours is inversely related to the homogeneity of the electric field, it is possible to optimize the design to minimize the curvature of the field lines. Consequently, in one approach, one or more of conditions (1)-(3) described above are met to increase the accuracy of the cylindrical model.

Figure 11A:
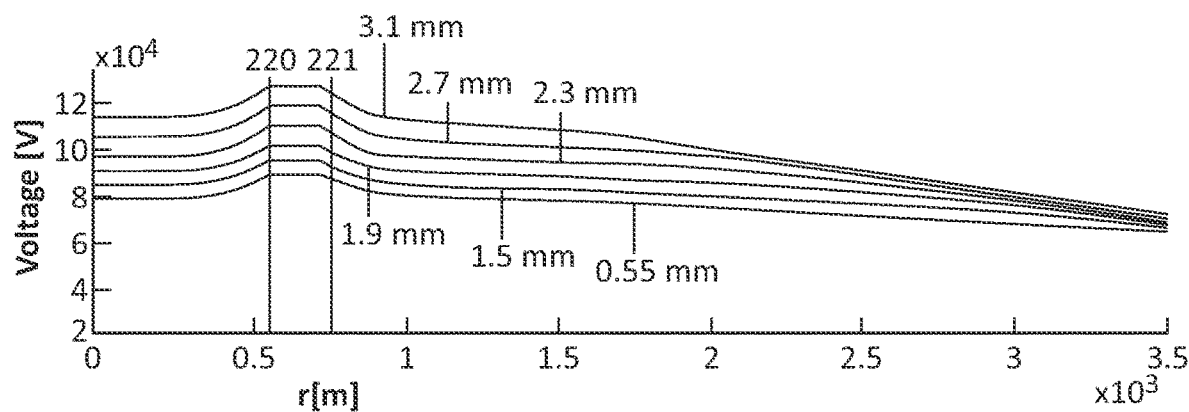
FIG. 11A shows the voltage recorded by a conductance catheter with a radius of 0.55 mm for various size vessels (vessel radii of 3.1, 2.7, 2.3, 1.9, 1.5 and 0.55 mm for the six curves, respectively) when a 0.5% NaCl bolus is injected into the treatment site.
Figure 11B:
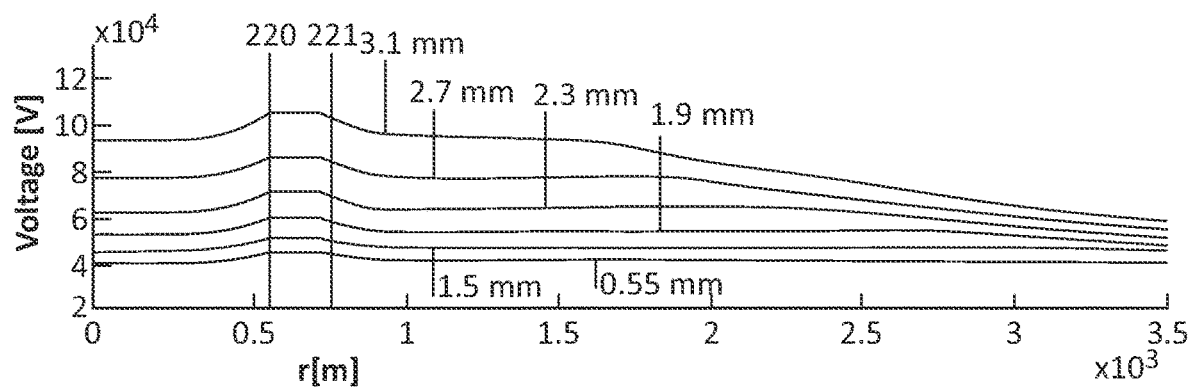
FIG. 11B shows the voltage recorded by a conductance catheter with a radius of 0.55 mm for various size vessels (vessel radii of 3.1, 2.7, 2.3, 1.9, 1.5 and 0.55 mm for the six curves, respectively) when a 1.5% NaCl bolus is injected into the treatment site.

Theoretically, it is impossible to ensure a completely homogeneous field given the current leakage through the lumen wall into the surrounding tissue. It was found that the iso-potential line is not constant as one moves out radially along the vessel as stipulated by the cylindrical model. FIGS. 11A and 11B show the detected voltage for a catheter with a radius of 0.55 mm for two different NaCl solutions (0.5% and 1.5%, respectively). The origin corresponds to the center of the catheter. The first vertical line 220 represents the inner part of the electrode which is wrapped around the catheter, and the second vertical line 221 is the outer part of the electrode in contact with the solution (diameter of electrode is approximately 0.25 mm). The six different curves, top to bottom, correspond to six different vessels with radii of 3.1 mm, 2.7 mm, 2.3 mm, 1.9 mm, 1.5 mm, and 0.55 mm, respectively. It can be seen that a "hill" 220, 221 occurs at the detection electrodes, followed by a fairly uniform plateau in the vessel lumen, followed by an exponential decay into the surrounding tissue. Since the potential difference is measured at the detection electrode 220, 221, the simulation generates the "hill" whose value corresponds to the equivalent potential in the vessel as used in Equation [5]. Thus, for each catheter size, the dimension of the vessel was varied such that Equation [5] was exactly satisfied. Consequently, the optimum catheter size for a given vessel diameter was obtained such that the distributive model satisfies the lumped equations (Equations [5] and [6]). In this way, a relationship between vessel diameter and catheter diameter can be generated such that the error in the CSA determination is less than 5%. In one embodiment, different diameter catheters are prepackaged and labeled for optimal use in certain size vessel. For example, for vessel dimensions in the range of 4 mm to 5 mm, 5 mm to 7 mm, or 7 mm to 10 mm, analysis shows that optimum diameter catheters will be in the range of 0.9 mm to 1.4 mm, 1.4 mm to 2 mm, or 2 mm to 4.6 mm, respectively. The clinician can select the appropriate diameter catheter based on the estimated vessel diameter of interest. This decision will be made prior to the procedure and will serve to minimize the error in the determination of lumen CSA.

Thus, a number of the embodiments disclosed herein accurately calculate lumen cross-sectional area by measuring conductance and correcting for various errors inherent in such measurements. However, at least some of the disclosed embodiments provide for the localization of body lumen junctions and other intraluminal anatomical structures using relative conductances and/or cross-sectional areas. Because only relative differences in conductance or cross-sectional area are necessary for accurate localization, the calculation of absolute values for various locations within the body lumen may be skipped in most instances.

Figure 9:
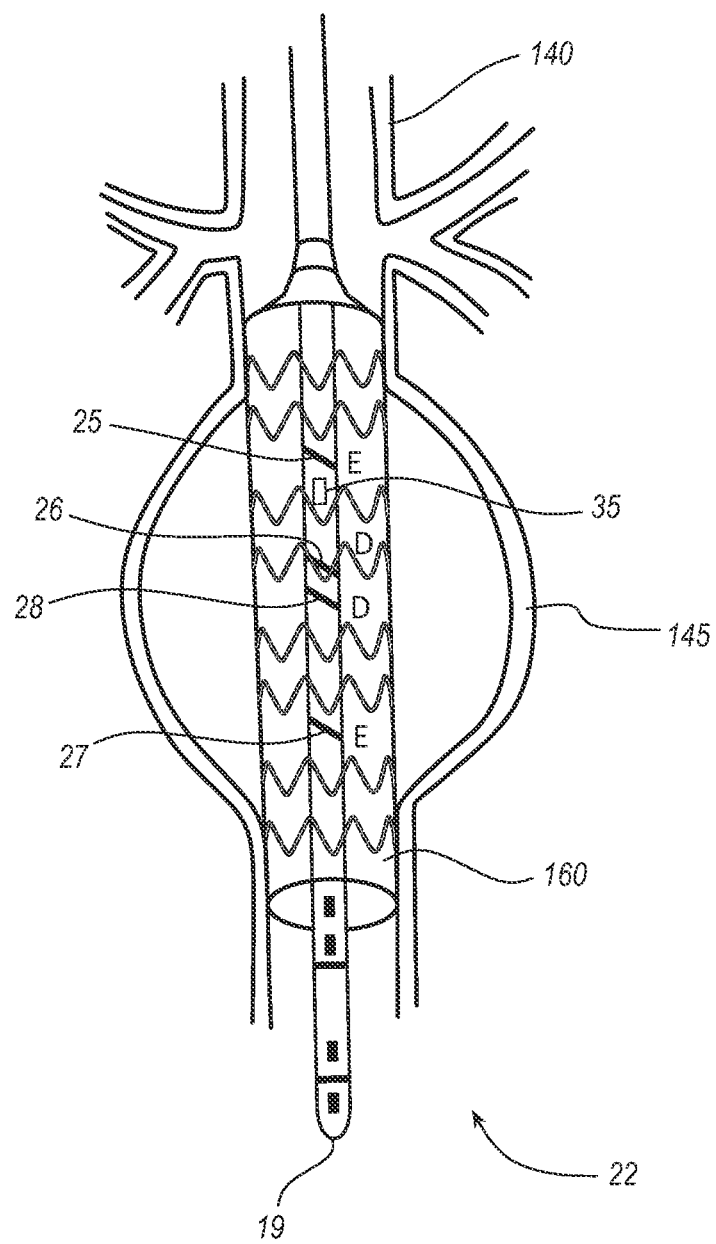
FIG. 9 shows one embodiment of a catheter for localization being used in the treatment of an aortic aneurysm.

Referring now to the embodiment shown in FIG. 9, one clinical application of catheter 22 is shown. Specifically, catheter 22 comprising stent 160 is positioned within an aorta 140 for the treatment of an aortic aneurysm 145. As described above with respect to FIG. 4A, a set of excitation electrodes 25, 27, and detection electrodes 26, 28 are located on catheter 22, which is disposed within stent 160.

In this embodiment, catheter 22, and thereby stent 160, is introduced into the blood stream percutaneously with a femoral approach. After the graft is routed into the aorta, electrodes 25, 26, 27, 28 are activated and electrical current flow is provided to the aortic lumen through the catheter 22 as previously described herein. In one embodiment, prior to or concurrent with collecting the conductance data, the catheter 22 may release fluid, such as a solution of NaCl having a known conductivity, into the aortic lumen, such that the fluid passing through the lumen comes into contact with the distal end of the electrodes 25, 26, 27, 28.

Conductance data is collected at a plurality of locations throughout the aorta 140 to determine a profile and cross-sectional area at various points along the aortic lumen. Further, any inherent errors in collected data can be corrected using any of the computational processes disclosed herein. In this manner, precise cross-sectional values of the aortic lumen can be obtained, as well as an accurate profile map of the region. Based on that data, the aneurysm can be precisely located within the aorta (e.g., where a larger conductance value is detected), and the stent 160 may be properly sized to affix to the aortic wall both distally and proximally of the aneurysm.

Figure 10:
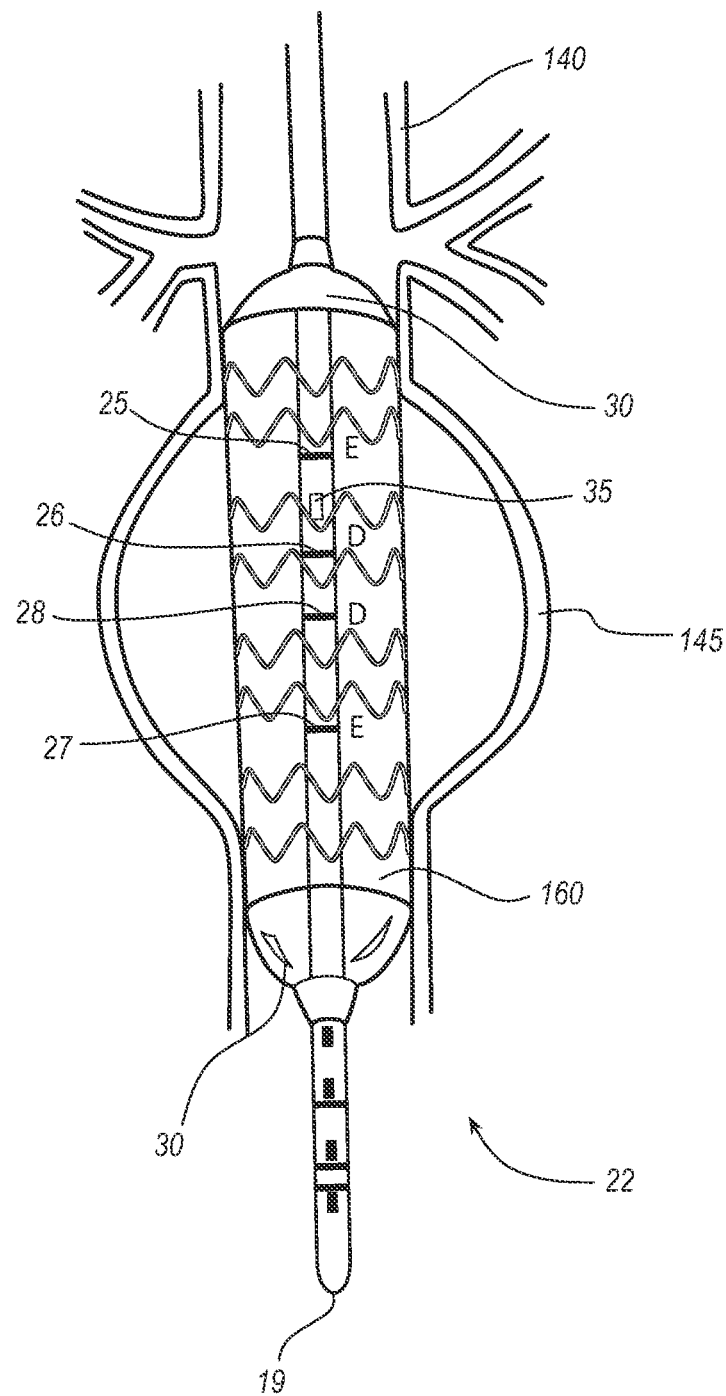
FIG. 10 shows one embodiment of a treatment for an aortic aneurysm.

Now referring to FIG. 10, a balloon 30 is used to distend stent 160 within the aneurytic region of the aorta 140. Inflation of the balloon 30 applies a force to the stent 160 which extends radially and presses into the vessel wall just above and just below the aneurysm. As noted with respect to the embodiment shown in FIG. 9, the profile and cross-sectional area of the aorta determined from the conductance data can be used to identify the optimal diameter to which the balloon 30 should be inflated. Accordingly, the stent 160 can be accurately sized to effectively treat the aneurysm. Furthermore, as the two necks of the graft should be deployed on an atherosclerosis-free aorta, the profile and cross-sectional area of the aorta determined from the conductance data can be used to identify a good landing zone for the deployment of the graft and thus prevent graft migration or endoleak.

While various embodiments of devices, systems, and methods for localization of body lumen junctures have been described in considerable detail herein, the embodiments are merely offered by way of non-limiting examples. Many variations and modifications of the embodiments described herein will be apparent to one of ordinary skill in the art in light of the disclosure. It will therefore be understood by those skilled in the art that various changes and modifications may be made, and equivalents may be substituted for elements thereof, without departing from the scope of the disclosure. Indeed, this disclosure is not intended to be exhaustive or to limiting. The scope of the disclosure is to be defined by the appended claims, and by their equivalents.

Further, in describing representative embodiments, the disclosure may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps disclosed herein should not be construed as limitations on the claims. In addition, the claims directed to a method and/or process should not be limited to the performance of their steps in the order written, and one skilled in the art can readily appreciate that the sequences may be varied and still remain within the spirit and scope of the present disclosure.

It is therefore intended that this description and the appended claims will encompass, all modifications and changes apparent to those of ordinary skill in the art based on this disclosure.

What is claimed is:

1. A method for generating a lumen profile, comprising:
   collecting conductance data detected at a plurality of locations along a body lumen with a pair of electrodes along an insertable portion of a catheter; and
   processing the conductance data with a processor, the processing step comprising:
   eliminating a first spike in conductance from the conductance data if the first spike is greater than a predefined threshold limit, thereby generating a first modified conductance data;
   applying a smoothing algorithm to the first modified conductance data to eliminate a second spike in conductance from the conductance data if the second spike is due to a bifurcation in the body lumen, thereby generating a second modified conductance data; and
   generating the lumen profile based on the second modified conductance data.

2. The method of claim 1, further comprising alternately exciting and detecting with each electrode of the pair of electrodes, a circuit including the pair of electrodes further including a delay for alternately exciting and detecting with the pair of electrodes.

3. The method of claim 1, wherein the catheter includes a second pair of electrodes, thereby obviating alternately exciting and detecting with any electrode of any pair of electrodes.

4. The method of claim 1, further comprising transmitting the conductance data detected by the pair of electrodes though a channel of the catheter including electrical wires connected to the pair of electrodes, across an adaptor interface, and to the processor for processing of the conductance data.

5. The method of claim 1, wherein the smoothing algorithm includes linear interpolation, cubic-spline interpolation, or both.

6. The method of claim 1, further comprising displaying the lumen profile on a display screen, the lumen profile comprising relative conductance values.

7. The method of claim 6, wherein processing the conductance data with the processor further comprises determining one or more intralumen anatomical structures from the relative conductance values.

8. The method of claim 1, further comprising displaying the lumen profile on a display screen, the lumen profile comprising relative luminal cross-sectional areas.

9. The method of claim 8, wherein processing the conductance data with the processor further comprises determining one or more intralumen anatomical structures from the relative luminal cross-sectional areas.

* * * * *